US012691147B2

(12) United States Patent
O'Heeron et al.

(10) Patent No.: US 12,691,147 B2
(45) Date of Patent: Jul. 28, 2026

(54) METHODS AND COMPOSITIONS FOR TREATMENT OF TYPE 1 DIABETES USING FIBROBLASTS AS FACILITATORS OF ISLET ENGRAFTMENT

(71) Applicant: FIBROBIOLOGICS, INC., Houston, TX (US)

(72) Inventors: Pete O'Heeron, Houston, TX (US); Thomas Ichim, San Diego, CA (US)

(73) Assignee: Fibrobiologics, Inc., Houston, TX (US)

( * ) Notice: Subject to any disclaimer, the term of this patent is extended or adjusted under 35 U.S.C. 154(b) by 1140 days.

(21) Appl. No.: 17/309,176

(22) PCT Filed: Nov. 4, 2019

(86) PCT No.: PCT/US2019/059666
§ 371 (c)(1),
(2) Date: May 3, 2021

(87) PCT Pub. No.: WO2020/093047
PCT Pub. Date: May 7, 2020

(65) Prior Publication Data

US 2022/0000934 A1     Jan. 6, 2022

Related U.S. Application Data

(60) Provisional application No. 62/755,523, filed on Nov. 4, 2018.

(51) Int. Cl.
| | |
|---|---|
| *A61K 35/33* | (2015.01) |
| *A61K 35/39* | (2015.01) |
| *A61K 35/44* | (2015.01) |
| *A61K 35/50* | (2015.01) |
| *A61P 3/08* | (2006.01) |

(52) U.S. Cl.
CPC ............. *A61K 35/33* (2013.01); *A61K 35/39* (2013.01); *A61K 35/44* (2013.01); *A61K 35/50* (2013.01); *A61P 3/08* (2018.01)

(58) Field of Classification Search
CPC ........ A61K 35/33; A61K 35/39; A61K 35/44; A61P 3/08
See application file for complete search history.

(56) References Cited

U.S. PATENT DOCUMENTS

| | | | |
|---|---|---|---|
| 7,491,388 B1 | 2/2009 | Mc Intosh et al. | |
| 7,651,855 B2 | 1/2010 | Blazar et al. | |
| 9,404,087 B2 * | 8/2016 | Revel | A61P 5/48 |
| 10,912,800 B2 * | 2/2021 | Evans | C12N 15/86 |
| 2007/0128174 A1 | 6/2007 | Kleinsek et al. | |
| 2009/0053182 A1 * | 2/2009 | Ichim | A61K 38/193 |
| | | | 435/366 |
| 2010/0092433 A1 * | 4/2010 | Levenberg | A61L 27/3886 |
| | | | 435/395 |
| 2012/0269774 A1 * | 10/2012 | Ichim | A61K 35/51 |
| | | | 424/93.7 |
| 2014/0356361 A1 | 12/2014 | Maldonado et al. | |
| 2017/0296588 A1 * | 10/2017 | Ichim | A61K 35/28 |
| 2018/0369290 A1 * | 12/2018 | Molakandov | C12N 5/0676 |
| 2020/0316134 A1 * | 10/2020 | Ricordi | A61K 38/4833 |

FOREIGN PATENT DOCUMENTS

| | | | | |
|---|---|---|---|---|
| CA | 2962655 A1 | 3/2016 | | |
| WO | 2018/013897 A1 | 1/2018 | | |
| WO | WO-2018183194 A1 * | 10/2018 | ............. | A61K 35/17 |
| WO | 2019/108756 A1 | 6/2019 | | |

OTHER PUBLICATIONS

Denu et al., (Acta Haematol. 2016;136(2):85-97. doi: 10.1159/000445096. May 18, 2016.) (Year: 2016).*
Ichim et al. (J Transl Med (2018) 16:212 https://doi.org/10.1186/s12967-018-1536-1) (Year: 2018).*
Covens et al. "Characterization of Proposed Human B-1 Cells Reveals Pre-Plasmablast Phenotype", Blood Journal, Jun. 27, 2013, vol. 121, No. 26, pp. 5176-5183.
De Masson et al. "CD24^hi CD27^+ and Plasmablast-Like Regulatory B Cells in Human Chronic Graft-Veersus-Host Disease", Blood, Mar. 12, 2005, vol. 125, No. 11, pp. 1830-1839.
Ashara, "Endothelial Progenitor Cells for Vascular Medicine," Yakugaku Zasshi, 127(5):841-845, 2007. (English abstract).
Office Communication issued in Japanese Patent Application No. 2021-524222, dated Jul. 28, 2023.
Sakata et al., "Bone Marrow Cell Cotransplantation with Islets Improves their Vascularization and Function," Transplantation, 89(6):686-693, 2010.
Extended European Search Report issued in European Patent Application No. 19878416.7, 11 pages, dated May 11, 2022.
Ichim et al., "Fibroblasts as a practical alternative to mesenchymal stem cells," Journal of Translational Medicine, 16(1):1-9, 2018.
Matsushima et al., "Human Fibroblast Sheet Promotes Human Pancreatic Islet Survival and Function in Vitro," Cell Transplantation, 25(8):1525-1527, 2016.

(Continued)

*Primary Examiner* — Christopher M Babic
*Assistant Examiner* — Joel D Levin
(74) *Attorney, Agent, or Firm* — Norton Rose Fulbright US LLP

(57) ABSTRACT

Embodiments of the disclosure pertain to the treatment of diabetes through replacement of insulin producing cells. In specific embodiments, the disclosure encompasses the use of cellular adjuvants to enhance survival, engraftment and tolerogenesis of insulin-producing cells. In certain cases the disclosure concerns the manipulation of a hepatic microenvironment to promote immunological tolerance at an enhanced level to allow for integration of allogeneic insulin-producing cells. Particular embodiments utilize fibroblasts to enhance immunological tolerance for insulin-producing cells upon engraftment.

9 Claims, 1 Drawing Sheet

(56)            References Cited

OTHER PUBLICATIONS

Perez-Basterrechea et al., "Fibroblasts accelerate islet revascularization and improve long-term graft survival in a mouse model of subcutaneous islet transplantation," PLOS One, 12(7):e0180695, 18 pages, 2017.

Perez-Basterrechea et al., "Plasma-Fibroblast Gel as Scaffold for Islet Transplantation," Tissue Engineering Part A, 15(3):569-577, 2009.

Perez-Basterrechea et al., "Cooperation by Fibroblasts and Bone Marrow-Mesenchymal Stem Cells to Improve Pancreatic Rat-to-Mouse Islet Xenotranslplantation," PLOS One, 8(8):e73526, 12 pages, 2013.

Quaranta et al., "Co-Transplantation of Endothelial Progenitor Cells and Pancreatic Islets to Induce Long-Lasting Normoglycemia in Steptozotocin-Treated Diabetic Rats," PLOS One, 9(4):e94783, 13 pages, 2014.

Denu et al., "Fibroblasts and Mesenchymal Stromal/Stem Cells Are Phenotypically Indistinguishable," Acta Haematol., 136:85-97, 2016.

English translation of Office Communication issued in Japanese Patent Application No. 2021-524222, dated Jun. 28, 2024.

* cited by examiner

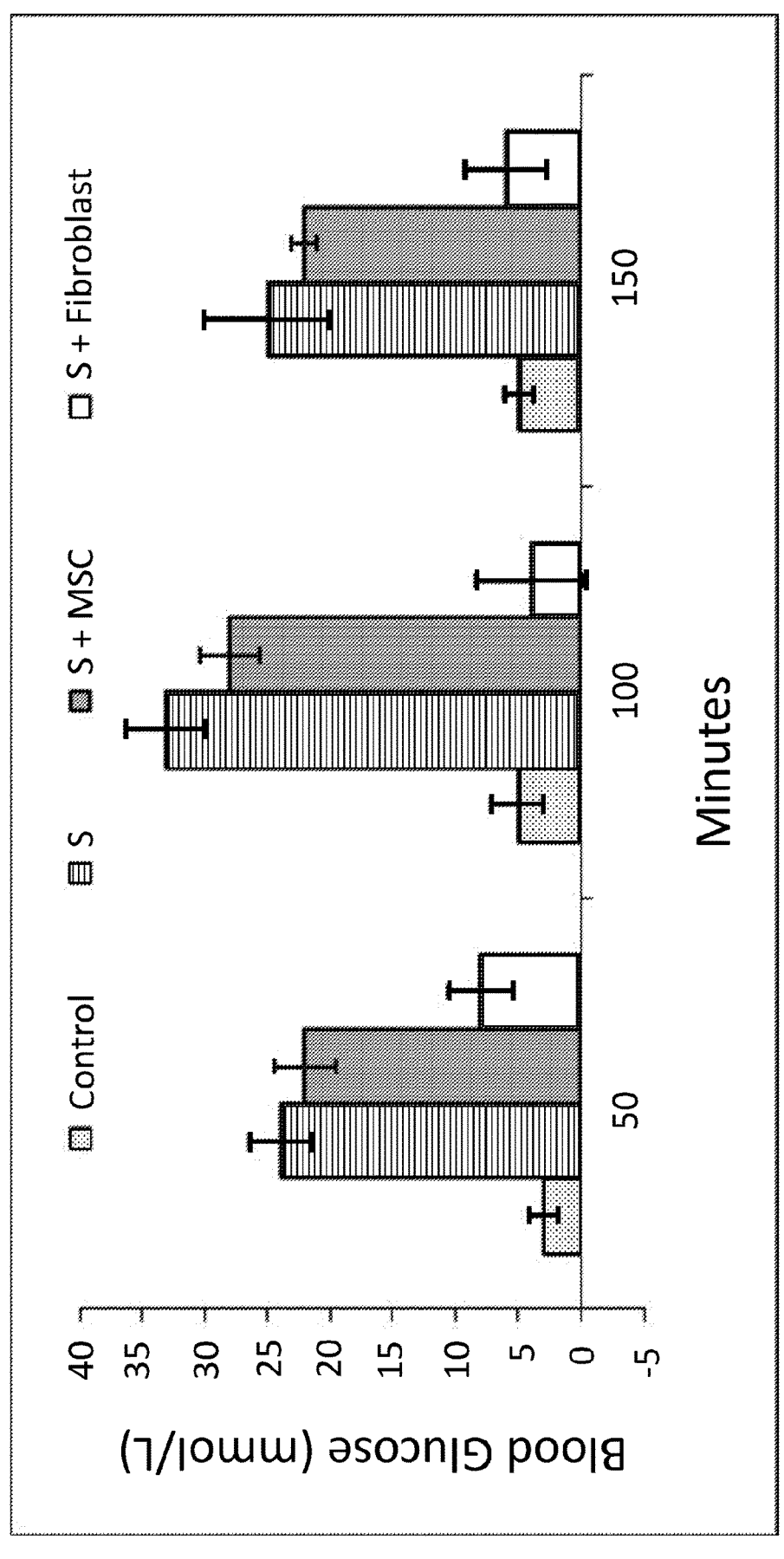

METHODS AND COMPOSITIONS FOR TREATMENT OF TYPE 1 DIABETES USING FIBROBLASTS AS FACILITATORS OF ISLET ENGRAFTMENT

This application is a national phase application under 35 U.S.C. § 371 that claims priority to International Application No. PCT/US2019/059666 filed Nov. 4, 2019, which claims priority to U.S. Provisional Patent Application Ser. No. 62/755,523, filed Nov. 4, 2018, both of which are incorporated by reference herein in their entirety.

TECHNICAL FIELD

Embodiments of the disclosure concern at least the fields of cell biology, molecular biology, physiology, and medicine, including diabetes medicine.

BACKGROUND

Type 1 diabetes is an autoimmune conditions that has traditionally been treated by life-long insulin therapy or pancreas transplantation. However, frequent episodes of hypoglycemia are common in patients on life-long insulin therapy and whole pancreas transplantation is an invasive surgical procedure with significant risks. Islet of Langerhans cell transplantation is an attractive alternative to the traditional treatments of type 1 diabetes. However, two of the major limiting factors in the widespread use of islet cell transplantation clinically are the availability of a sufficient number of islets and the inability of current immunosuppressive treatments to protect transplanted islets long-term. Despite this, islet transplantation has revolutionized the treatment of type 1 diabetes in the sense that "cure" has been achieved in some patients [1]. Drawbacks of islet transplantation include need in for multiple donors [2], lack of stable engraftment (5 years only 10% still have graft)[3], and need for continual immune suppression [4]. Various strategies have been used to enhance engraftment but major clinical success has not been seen. Many immunosuppressive protocols used in islet cell transplantation to date have relied on calcineurin inhibitors that have been shown to negatively affect pancreatic beta cell function and insulin sensitivity. Therefore, despite offering protection from host immune attack, these agents themselves can diminish graft function and contribute to failure of the transplanted islets. Additionally, recipients of islet grafts still demonstrate the autoimmune effects of diabetes development that led to their disease initially, thereby affecting function of transplanted islets long-term.

The present disclosure satisfies a long-felt need in the art for diabetes treatment.

BRIEF SUMMARY

Embodiments of the disclosure encompass methods and compositions related to cell therapy, including at least cell transplant and allograft therapy. In specific aspects, the methods and compositions facilitate transplant of certain types of cells to be transplanted, including at least cells that are beneficial to the treatment of diabetes, for example. In at least some cases, combination therapies of different cell types facilitate acceptance and immune tolerance of another type of cells. In specific embodiments, fibroblasts (alone or in combination with other cells) facilitate the effective transplant of pancreatic islet cells.

Disclosed in particular are means of enhancing engraftment, viability and function of pancreatic islet allografts in a hepatic microenvironment, for example through co-administration of (1) allogeneic endothelial progenitor cells (EPC), and/or (2) allogeneic fibroblasts. In one embodiment of the disclosure, the hepatic microenvironment is primed by administration of EPC (and/or supernatants secreted by the EPC) followed by, during, or subsequent to administration of fibroblasts; such priming facilitates modulating a hepatic microenvironment at least in order to suppress initial inflammatory or "danger" signals and allow for tolerogenesis and integration of islet allograft. Administration of allogeneic EPC may be performed in conjunction with grafting of islets or grafting of islet cells, as well as fibroblast administration. In one embodiment, allogeneic fibroblasts are administered (for example, intraportally) subsequent, during, and/or prior to EPC administration to support engraftment of allogeneic EPC, which eventually allows for endogenous EPC to surround the allogeneic islet graft(s) and hence allow for a reduced amount of donor material needed for transplantation. In specific embodiments, in some cases allogeneic EPC are engrafted and in some cases islet cells (or islets) are engrafted, or both.

Embodiments of the disclosure encompass methods of enhancing survival of allogeneic or autologous insulin-producing cells in an individual, comprising the steps of administering an effective amount of endothelial progenitor cells (EPCs) and/or fibroblasts prior to, concurrent with, and/or subsequent to transplantation of said allogeneic or autologous insulin-producing cells in the individual. In specific cases, the fibroblasts and/or EPCs are allogeneic to the individual. The allogeneic insulin-producing cells may be derived from a pancreatic donor. The allogeneic insulin-producing cells may be comprised of islet cell mass. The allogeneic insulin producing cells may be derived from in vitro differentiation from a population of progenitor cells. In particular cases, the EPCs express markers selected from the group consisting of: a) flk-1; b) CD31; c) CD34; d) CD133; f) PDGF-R; g) hTERT; and h) a combination thereof. The EPC may be derived by a method comprising the steps of: (i) isolating a mammalian cellular population; (ii) enriching for a subpopulation of the cells of step (i), which subpopulation expresses a CD45$^-$ phenotypic profile; (iii) enriching for a subpopulation of the CD45$^-$ cells derived from step (ii) which express a CD34$^+$ phenotypic profile; and (iv) isolating the subpopulation of CD34$^+$ cells derived from step (iii) which express a CD31$^{lo/-}$ phenotypic profile, to thereby isolate the endothelial progenitor cells. The EPC may be derived from placental tissues, bone marrow, adipose tissue, omentum, or a combination thereof. The placentally-derived EPC may be of fetal origin. The fibroblast cells may be capable of differentiation into the chondrocytic lineage. In specific cases, the fibroblast cell expresses one or more markers selected from the group consisting of a) NANOG; b) OCT-4; c) SSEA-4; d) stem cell factor receptor; and e) a combination thereof. In specific cases, the fibroblasts cell are isolated by a method comprising the steps of: (i) isolating a mammalian cellular population; (ii) enriching for a subpopulation of the cells of step (i), which subpopulation expresses a CD45$^-$ phenotypic profile; and (a) enriching for a subpopulation of the CD45$^-$ cells derived from step (ii) which express a CD34$^+$ phenotypic profile and isolating the subpopulation of said CD34$^+$ cells to thereby isolate fibroblast cells with regenerative properties. Fibroblasts utilized in methods of the disclosure may be derived from one or more tissue sources selected from the group consisting of a) foreskin; b) tummy tucks; c) placenta; d) ear lobe; e) adipose tissue; f) omentum; g) wharton's jelly; and h) a combination thereof. Placental fibroblast cells when used may be derived from fetal side of the placenta. In specific embodiments, the CD45 negative fibroblasts are fetally-derived. The fibroblast cells may be purified for expression of one or more markers of regenerative potential using methods selected from the group consisting of a) magnetic activated cell sorting; b) flow cytometry sorting; c) cellular panning; d) an affinity based means to selectively select cells of regenerative potential; e) a size based means to select for cells possessing regenerative potential; and f) a combination thereof.

In one embodiment, there is a method of stimulating in an individual a tolerogenic immune response to one or more antigens associated with insulin producing cells, said method comprising the step of administering an effective amount of allogeneic insulin producing cells, allogeneic EPC, and allogeneic fibroblasts. In alternative cases, one or more of the insulin producing cells, EPC, and fibroblasts are autologous to the individual. In specific embodiments, the tolerogenic response comprises stimulation of antigen-specific T regulatory cells. The T regulatory cells may possess the ability to inhibit cells that kill or suppress activity of insulin producing cells. In specific embodiments, the T regulatory cells express the transcription factor FoxP3. In specific embodiments, the tolerogenic response comprises stimulation of antigen-specific B regulatory cells, such as B regulatory cells that express CD10. The B regulatory cells may be proplasmablasts.

The foregoing has outlined rather broadly the features and technical advantages of the present disclosure in order that the detailed description that follows may be better understood. Additional features and advantages will be described hereinafter which form the subject of the claims herein. It should be appreciated by those skilled in the art that the conception and specific embodiments disclosed may be readily utilized as a basis for modifying or designing other structures for carrying out the same purposes of the present designs. It should also be realized by those skilled in the art that such equivalent constructions do not depart from the spirit and scope as set forth in the appended claims. The novel features which are believed to be characteristic of the designs disclosed herein, both as to the organization and method of operation, together with further objects and advantages will be better understood from the following description when considered in connection with the accompanying figures. It is to be expressly understood, however, that each of the FIGURES is provided for the purpose of illustration and description only and is not intended as a definition of the limits of the present disclosure.

BRIEF DESCRIPTION OF THE DRAWINGS

For a more complete understanding of the present disclosure, reference is now made to the following descriptions taken in conjunction with the accompanying drawing.

FIG. 1 demonstrates blood glucose levels in the presence of no Streptozocin (Control); Streptozocin (S); Streptozocin+bone marrow mesenchymal stem cells (S+MSC) and Streptozocin+Fibroblast selected for CD73 (S+Fibroblast) (from left to right).

DETAILED DESCRIPTION

As used herein the specification, "a" or "an" may mean one or more. As used herein in the claim(s), when used in conjunction with the word "comprising", the words "a" or "an" may mean one or more than one. As used herein "another" may mean at least a second or more. In specific embodiments, aspects of the invention may "consist essentially of" or "consist of" one or more sequences of the invention, for example. Some embodiments of the invention may consist of or consist essentially of one or more elements, method steps, and/or methods of the invention. It is contemplated that any method or composition described herein can be implemented with respect to any other method or composition described herein.

In keeping with long-standing patent law convention, the words "a" and "an" when used in the present specification in concert with the word comprising, including the claims, denote "one or more." Some embodiments of the disclosure may consist of or consist essentially of one or more elements, method steps, and/or methods of the disclosure. It is contemplated that any method or composition described herein can be implemented with respect to any other method or composition described herein embodiments which are disclosed and still obtain a like or similar result without departing from the spirit and scope of the disclosure. The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the terms "or" and "and/or" are utilized to describe multiple components in combination or exclusive of one another. For example, "x, y, and/or z" can refer to "x" alone, "y" alone, "z" alone, "x, y, and z," "(x and y) or z," "x or (y and z)," or "x or y or z." It is specifically contemplated that x, y, or z may be specifically excluded from an embodiment.

Throughout this application, the term "about" is used according to its plain and ordinary meaning in the area of cell and molecular biology to indicate that a value includes the standard deviation of error for the device or method being employed to determine the value.

"Subject" and "patient" and "individual" refer to either a human or non-human, such as primates, mammals, and vertebrates. In particular embodiments, the subject is a human, dog, cat, horse, cow, and so forth.

"Treating" or treatment of a disease or condition refers to executing a protocol, which may include administering one or more drugs or therapies (including cells) to a patient, in an effort to alleviate at least one sign or symptom of the disease. Desirable effects of treatment include decreasing the rate of disease progression, ameliorating or palliating the disease state, delaying the onset of at least one symptom, and remission or improved prognosis. Alleviation can occur prior to signs or symptoms of the disease or condition appearing, as well as after their appearance, or both. Thus, "treating" or "treatment" may include "preventing" or "prevention" of disease or undesirable condition. In addition, "treating" or "treatment" does not require complete alleviation of one or more signs or symptoms, does not require a cure, and specifically includes protocols that have only a marginal effect on the patient.

As used herein, "prevent," and similar words such as "prevented," "preventing" etc., indicate an approach for preventing, inhibiting, or reducing the likelihood of the occurrence or recurrence of, a disease or condition, e.g., cancer. It also refers to delaying the onset or recurrence of a disease or condition or delaying the occurrence or recurrence of the symptoms of a disease or condition. As used herein, "prevention" and similar words also includes reducing the intensity, effect, symptoms and/or burden of a disease or condition prior to onset or recurrence of the disease or condition.

The term "pharmaceutically" or "pharmacologically acceptable", as used herein, refer to molecular entities and compositions that do not produce adverse, allergic, or other untoward reactions when administered to an animal or a human.

The term, "pharmaceutically acceptable carrier", as used herein, includes any and all solvents, or a dispersion medium including, but not limited to, water, ethanol, polyol (for example, glycerol, propylene glycol, and liquid polyethylene glycol, and the like), suitable mixtures thereof, and vegetable oils, coatings, isotonic and absorption delaying agents, liposome, commercially available cleansers, and the like. Supplementary bioactive ingredients also can be incorporated into such carriers.

I. Examples of Definitions

Cell culture refers generally to cells taken from a living organism and grown under controlled condition ("in culture" or "cultured"). A primary cell culture is a culture of cells, tissues, or organs taken directly from an organism(s) before the first subculture. Cells are expanded in culture when they are placed in a growth medium under conditions that facilitate cell growth and/or division, resulting in a larger population of the cells. When cells are expanded in culture, the rate of cell proliferation is sometimes measured by the amount of time needed for the cells to double in number, referred to as doubling time.

A cell line is a population of cells formed by one or more subcultivations of a primary cell culture. Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but not limited to the seeding density, substrate, medium, growth conditions, and time between passaging.

A conditioned medium is a medium in which a specific cell or population of cells has been cultured and then removed. When cells are cultured in a medium, they may secrete cellular factors that can provide trophic support to other cells. Such trophic factors include, but are not limited to hormones, cytokines, extracellular matrix (ECM), proteins, vesicles, antibodies, and granules. The medium containing the cellular factors is the conditioned medium. In some embodiments the invention teaches the use of conditioned media, or concentrated conditioned media, or exosomes isolated from conditioned media of EPC or fibroblasts to promote tolerogenesis.

As used herein, the term "growth medium" generally refers to a medium sufficient for the culturing of umbilicus-derived cells. In particular, one particular medium for the culturing of the cells of the invention herein comprises Dulbecco's Modified Essential Media (also abbreviated DMEM herein). Particularly preferred is DMEM-low glucose (also DMEM-LG herein) (Invitrogen, Carlsbad, Calif.). The DMEM-low glucose is preferably supplemented with 15% (v/v) fetal bovine serum (e.g. defined fetal bovine serum, Hyclone, Logan Utah), antibiotics/antimycotics (preferably penicillin (100 Units/milliliter), streptomycin (100 milligrams/milliliter), and amphotericin B (0.25 micrograms/milliliter), (Invitrogen, Carlsbad, Calif.)), and 0.001% (v/v) 2-mercaptoethanol (Sigma, St. Louis Mo.). In some cases different growth media are used, or different supplementations are provided, and these are normally indicated in the text as supplementations to Growth Medium.

Also relating to the present disclosure, the term "standard growth conditions", as used herein refers to culturing of cells at 37° C., in a standard atmosphere comprising 5% $CO_2$. Relative humidity is maintained at about 100%. While foregoing the conditions are useful for culturing, it is to be understood that such conditions are capable of being varied by the skilled artisan who will appreciate the options available in the art for culturing cells, for example, varying the temperature, $CO_2$, relative humidity, oxygen, growth medium, and the like.

"Fibroblasts" in some embodiments refers to cells that are (1) adherent to plastic, (2) express CD73, CD90, and CD105 antigens, while being CD14, CD34, CD45, and HLA-DR negative, and (3) possess ability to differentiate to at least one of the following three lineages: osteogenic, chondrogenic and adipogenic lineage. Other cells possessing fibroblast-like properties are included within the definition of "fibroblasts", with the condition that the cells possess at least one of the following (at least in some cases): a) regenerative activity; b) production of growth factors; c) ability to induce a healing response, either directly, or through elicitation of endogenous host repair mechanisms. Fibroblasts can be derived from any tissue including, but not limited to, bone marrow, adipose tissue, amniotic fluid, endometrium, tro-phoblast-derived tissues, cord blood, Wharton jelly, pla-centa, amniotic tissue, derived from pluripotent stem cells, and tooth, for example. In some definitions of "fibroblasts", the cells encompass cells that are CD34 positive upon initial isolation from tissue but are similar to cells described about phenotypically and functionally. As used herein, "fibro-blasts" may include cells that are isolated from tissues using cell surface markers selected from the following list: NGF-R, PDGF-R, EGF-R, IGF-R, CD29, CD49a, CD56, CD63, CD73, CD105, CD106, CD140b, CD146, CD271, MSCA-1, SSEA4, STRO-1 and/or STRO-3 or any combination thereof either before, during or after expansion.

II. General Embodiments

Embodiments of the disclosure encompass improvements of cell engraftment (including allogeneic cell engraftment) for a mammalian individual, including human, dog, cat, horse, and so forth. Improvements include at least the ability to have greater immunotolerance in vivo for the grafted cell population administered to the individual. In particular embodiments, allogeneic or autologous endothelial progeni-tor cells (EPC) and/or allogeneic or autologous fibroblasts allow for improved allogeneic islet engraftment. In specific embodiments, allogeneic endothelial progenitor cells (EPC), such as placentally-derived EPC of fetal origin, may be administered (for example, intraportally) without immediate rejection, and the EPC cells alone or together with fibro-blasts modulate an hepatic microenvironment to allow for enhanced allogeneic islet engraftment.

Although EPCs have been previously used in an autolo-gous fashion to support engraftment of islets [5], these were only animal studies, and practically EPC are difficult to use in an autologous manner, especially in diabetics in which EPC are compromised as a result of the underlying pathol-ogy [6, 7]. As such, the present disclosure provides means of using EPC (including placentally-derived) and fibroblasts as facilitators of islet engraftment. In one embodiment, the EPC cells and/or islets and/or islet cells are administered locally or systemically (including by injection and, in some cases, intraportally) to exploit the naturally occurring mechanism of intraportal tolerogenesis, which has been previously demonstrated by administration of various cells of immunogenic origin intraportally [8]. In one embodiment of the disclosure, the EPC and the fibroblasts are both allogeneic and are of the same donor origin. In a particular embodiment, fibroblasts are initially administered (for example, intraportally) to stimulate a tolerogenic event, followed by administration of EPC, although the fibroblasts may also or instead of be delivered with and/or after administration of EPC.

III. Methods of Use

Embodiments of the disclosure include methods of using fibroblasts to enhance engraftment of islets in an individual in need thereof. Although use of the fibroblasts to enhance islet engraftment may occur by any means, in specific embodiments the fibroblasts to suppress deleterious immune system reaction(s) to the islet graft. The suppression or lessening of the immune reaction occurs in the liver, in specific embodiments. In particular embodiments, EPCs are utilized in conjunction with fibroblasts to prime part of the liver to enhance the viability and function of the islet graft; such an effect may occur because of the angiogenic effect of the EPCs and/or their ability to act as tolerogenic antigen presenting cells. As used herein, "islet graft" refers to any collection of any kind of pancreatic islet of Langerhans cells.

Within the scope of the current disclosure is the consid-eration that fibroblasts possess similar properties to mesen-chymal stem cells in terms of immune modulation such that their use may be for analogous to fibroblasts. Accordingly, the known properties of MSC in order to provide one practicing the methods of the disclosure are herein extrapo-lated from MSC to fibroblasts. Some of the immune sup-pressive effects of MSC appear to be inducible by the presence of local inflammation. For example, a recent study showed that TLR activation on MSC increases ability of the MSC to suppress T cell activation through blockade of DC maturation [17]. Other studies have shown that treatment of MSC with inflammatory mediators such as IL-1 beta actu-ally stimulates production of cytokines such as IL-10 that block DC maturation. IL-1 treated MSC possess superior in vivo ability to suppress inflammatory diseases such as DSS induced colitis [18]. Similar augmentation of anti-inflam-matory activity of MSC by pretreatment with inflammatory cytokines was also reported by treatment with IFN-gamma [19-21]. On a cellular level it has been reported that co-culture of MSC with monocytes leads to enhanced immune suppressive activities of the MSC, in part through monocyte produced IL-1 [22]. Inhibition of T cell reactivity by MSC has been widely described. One of the initial publications supporting this assessed baboon MSCs in vitro for their ability to elicit a proliferative response from allogeneic lymphocytes, to inhibit an ongoing allogeneic response, and to inhibit a proliferative response to potent T-cell mitogens. It was found that the MSCs failed to elicit a proliferative response from allogeneic lymphocytes. MSCs added into a mixed lymphocyte reaction, either on day 0 or on day 3, or to mitogen-stimulated lymphocytes, led to a greater than 50% reduction in proliferative activity. This effect could be maximized by escalating the dose of MSCs and could be reduced with the addition of exogenous IL-2. In vivo admin-istration of MSCs led to prolonged skin graft survival when compared to control animals [23, 24]. Inhibition of T cell proliferation could not be restored by costimulation or pretreatment of the MSC with IFN-gamma [25], which is intriguing given that the previous study mentioned showed IL-2 could overcome MSC mediated suppression. In vivo studies using humanized mice demonstrated that human MSC were capable of suppressing human T cell responses in vivo, both allogenic and antigen-specific responses [26]. Inhibition of T cell activity seems to be not limited to proliferation but also was demonstrated to include suppres-sion of cytotoxic activity of CD8 T cells [27, 28]. Several mechanisms have been reported for MSC suppression of T cell activation including inhibition of IL-2 receptor alpha (CD25) [29], induction of division arrest [30, 31], induction of T cell anergy directly [32] or via immature DC [33], stimulation of apoptosis of activated T cells [34, 35], block-ade of IL-2 signaling and induction of PGE2 production [36-41], induction of TGF-beta[42], production of HLA-G [43], expression of serine protease inhibitor 6 [44], stimu-lation of nitric oxide release [45-47], stimulation of indola-mine 2,3 deoxygenase [48-51], expression of adenosine generating ectoenzymes such as CD39 and CD73 [52, 53], Galectin expression[54, 55], induction of hemoxygenase 1[56, 57], activation of the PD1 pathway [54, 58-60], Fas ligand expression [61, 62], CD200 expression [63], Th2 deviation [64-66], inhibition of Th17 differentiation [67-71], TSG-6 expression [72], NOTCH-1 expression [73], and stimulation of Treg cell generation [74-81].

Thus, in particular embodiments, a plurality of fibroblasts and a plurality of EPCs are utilized for individuals that are the subject of islet engraftment. The individual in receipt of the fibroblasts and/or EPCs may be diabetic, pre-diabetic, or at risk for diabetes (such as a family or personal history), for example. The use of the combinations of fibroblasts and EPCs provides for an improved ability for the graft to be successful in the individual. Although the fibroblasts and EPCs may be administered by any route and to any location, in specific cases both the fibroblasts and EPCs are administered to the same location, including the location of the islet engraftment or eventual location of the islet engraftment. In some cases, the location of administration is inherently pro-tolerogenic.

The combination of fibroblasts administered in an environment that is already pro-tolerogenic (for example, intraportal) enhances tolerogenicity, however for the practice of the disclosure the augmentation of tolerance may be supported by the administration of allogeneic EPC, which provide not only direct angiogenic support, but also act as tolerogenic antigen presenting cells. The EPCs may be alternative to the fibroblasts, in alternative embodiments. For the practice of the methods of the disclosure, below are different ways in which fibroblasts modulate the immune system such that a practitioner of the methods of the disclosure may utilize known means in the art. For example, fibroblasts modulate dendritic cell activity. Dendritic cells (DC) are considered the primary sentinels of the immune response, playing a key role in determining whether productive immunity will ensure, versus stimulation of T regulatory cells and suppression of immunity [9, 10]. Although various subtypes of DC exist, with varying specialized functions, one of the common themes appears to be that immature myeloid type DC reside in an immature state in the periphery, which engulf antigens and present in a tolerogenic manner to T cells in the lymph nodes. This is one of the mechanisms by which self-tolerance is maintained. Specifically, although small numbers of autoreactive T cells escape the thymic selection process, these T cells are either anergized, or their activity suppressed by T regulatory cells generated as a result of immature dendritic cells presenting self antigens to autoreactive T cells. In contrast, in the presence of "danger" signals, such as toll like receptor agonists, immature DC take a mature phenotype, characterized by high expression of costimulatory molecules, and subsequently induce T cell activation [11-13]. In the context of T1D it has previously been demonstrated that targeting of diabetogenic autoantigens to immature DC leads to prevention of disease [14]. Administration of immature DC into 10 T1D patients resulted in increased C-peptide levels with some evidence of immunomodulatory activity[15].

In some embodiments of the disclosure, there are methods of enhancing glucose control by islets co-transplanted with fibroblasts. In specific cases, fibroblasts are administered the islet cells (allogeneic or autologous) to an individual in need thereof. The fibroblasts may or may not have one or more specific markers, such as CD73, for example.

In one embodiment of the disclosure, fibroblasts are utilized to maintain DC in an immature state. Specifically, administration of fibroblasts together with DC enhances tolerogenesis. Given the role of DC in controlling immunity versus tolerance, the manipulation of DC maturation by fibroblasts would strongly support an immune modulatory role of fibroblasts. Early studies suggested that fibroblasts may inhibit the ability of DC to stimulate CD4 and CD8 cells using in vitro systems, however, it was demonstrated that fibroblasts also inhibited T cell activation directly [16].

In a particular embodiment, there is a method of enhancing survival of allogeneic insulin producing cells (that may be derived from a pancreatic donor or derived from in vitro differentiation from a population of progenitor cells and/or that are comprised of islet cell mass) in an individual comprising the steps of providing to the individual an effective amount of allogeneic EPC and allogeneic fibroblasts. In one embodiment of the disclosure, there is a method of enhancing survival of allogeneic insulin producing cells in an individual (that may be derived from a pancreatic donor or derived from in vitro differentiation from a population of progenitor cells and/or that are comprised of islet cell mass) comprising the steps of: a) obtaining a population of allogeneic endothelial progenitor cells (EPC); b) obtaining a population of allogeneic fibroblasts; and c) administering the allogeneic EPC and the allogeneic fibroblasts prior to, and/or concurrent with and/or subsequent to transplantation of the allogeneic insulin producing cells. The allogeneic EPC may or may not express markers selected from the group consisting of: a) flk-1; b) CD31; c) CD34; d) CD133; f) PDGF-R; g) hTERT; and h) a combination thereof. The allogenic EPC may be derived by a method comprising the steps of: (i) isolating a mammalian cellular population; (ii) enriching for a subpopulation of the cells of step (i), which subpopulation expresses a CD45$^-$ phenotypic profile; (iii) enriching for a subpopulation of the CD45$^-$ cells derived from step (ii) which express a CD34$^+$ phenotypic profile; and (iv) isolating the subpopulation of CD34$^+$ cells derived from step (iii) which express a CD31$^{lo/-}$ phenotypic profile, to thereby isolate the endothelial progenitor cells. The allogeneic EPC may be derived from placental tissues; bone marrow; adipose tissue; omentum, or placentally derived EPC are of fetal origin.

In one embodiment, there is a method of stimulating a tolerogenic immune response to antigens associated with insulin producing cells, the method comprising the step of administering an effective amount of allogeneic insulin producing cells together with allogeneic EPC and allogeneic fibroblasts. The tolerogenic response may comprise of stimulation of antigen specific T regulatory cells, and the T regulatory cells may possess the ability to inhibit cells that kill or suppress activity of insulin producing cells. The T regulatory cells may or may not express the transcription factor FoxP3. In a specific embodiment, the tolerogenic response comprises of stimulation of antigen specific B regulatory cells, and the B regulatory cells may or may not express CD10 and may or may not be proplasmablasts.

In one embodiment of the disclosure, fibroblasts of the same donor as a pancreatic allograft are administered (for example, intraportally and/or systemically) to the individual in order to induce a donor-specific tolerogenic event. In another embodiment, fibroblasts are obtained and/or generated from a donor and placed in an immunoisolatory chamber to induce tolerogenesis. In another embodiment, donor-specific fibroblasts and/or dendritic cells (DC) are administered together in the individual. In cases wherein DC are administered, the DC may be treated in a manner to prevent activation or upregulation of costimulatory molecule(s). One may treat with inhibitors of dendritic cell maturation, such as IL-10, aspirin, NF-kappa B inhibitors, and inhibitors of toll like receptors and downstream signaling of TLR. The fibroblasts and/or DC may be derived from any source, including bone marrow, peripheral blood, cadaveric bone marrow, or they may be generated by means of iPS technology, for example.

In cases wherein an effective amount of fibroblasts and EPCs are administered to an individual to enhance engraftment of insulin-producing cells (that may be pancreatic islet cells), the order in which the different cells are administered to the individual may be of any kind. In some cases, the fibroblasts are administered before the EPCs, whereas in other cases the fibroblasts are administered after the EPCs. The fibroblasts may be administered at the same time as the EPCs. In some cases, the islet cell engraftment occurs prior to the administration of the fibroblasts and/or the EPCs, whereas in other cases the islet cell engraftment occurs after the administration of the fibroblasts and/or the EPCs. The administration route of the fibroblasts may or may not be the same as the EPCs.

The effective amount of the fibroblasts may be of any kind and may be determined by a clinician, although in specific embodiments the amount is in the range of $10^4$ to $10^8$ fibroblasts cells/kg of recipient mass per administration. In some embodiments the optimal dose per administration will be between $10^5$ to $10^7$ fibroblasts cells/kg. In many embodiments the optimal dose per administration will be $5\times10^5$ to $5\times10^6$ fibroblasts cells/kg. The effective amount of the EPCs may be of any kind and may be determined by a clinician. In some cases, a particular ratio of fibroblasts to EPCs are utilized in the administration of the different cells. As an example, the ratio of fibroblasts to EPCs may be 1:1; 1:2; 1:10; 1:25; 1:50; 1:100; 1:1000; and so forth. As another example, the ratio of EPCs to fibroblasts may be 1:1; 1:2; 1:10; 1:25; 1:50; 1:100; 1:1000; and so forth.

In some embodiments fibroblasts are administered to a subject in one dose. In others, fibroblasts are administered to a subject in a series of two or more doses in succession. In some other embodiments wherein fibroblasts are administered in a single dose, in two doses, and/or more than two doses, the doses may be the same or different, and they may be administered with equal or with unequal intervals between them.

Fibroblasts and/or EPCs may be administered in many frequencies over a wide range of times. In some embodiments, fibroblasts and/or EPCs are administered over a period of less than one day. In other embodiments, they are administered over two, three, four, five, or six days. In some embodiments, fibroblasts and/or EPCs are administered one or more times per week, including over a period of weeks in some cases. In other embodiments they are administered over a period of weeks for one to several months. In various embodiments they may be administered over a period of months. In others they may be administered over a period of one or more years. Generally lengths of treatment are proportional to the length of the disease process, the effectiveness of the therapies being applied, and the condition and response of the subject being treated. It is to be appreciated that a single dose of cells may be delivered all at once, fractionally, or continuously over a period of time. The entire dose also may be delivered to a single location or spread fractionally over several locations. Suitable regimens for initial administration and subsequent doses or for sequential administrations may all be the same or may be variable. Appropriate regimens can be ascertained by the skilled artisan, from this disclosure, the documents cited herein, and the knowledge in the art.

In various embodiments, fibroblasts and/or EPCs may be administered in an initial dose, and thereafter maintained by further administration of fibroblasts and/or EPCs. Fibroblasts and/or EPCs may be administered by one method initially, and thereafter administered by the same method or one or more different methods. The subject's fibroblast levels can be maintained by the ongoing administration of the cells. Various embodiments encompass administration of the fibroblasts either initially or to maintain their level in the subject, or both, and in specific examples it may be by intravenous injection. In a variety of embodiments, other forms of administration are used dependent upon the individual's condition and other factors, discussed elsewhere herein.

It is noted that human subjects are treated generally longer than experimental animals; but, treatment generally has a length proportional to the length of the disease process and the effectiveness of the treatment. Those skilled in the art will take this into account in using the results of other procedures carried out in humans and/or in animals, such as rats, mice, non-human primates, and the like, to determine appropriate doses for humans. Such determinations, based on these considerations and taking into account guidance provided by the present disclosure and the prior art will enable the skilled artisan to do so without undue experimentation.

The dose, frequency, and/or duration of treatment may depend on factors, including the nature of the disease, the subject, and other therapies that may be administered. Accordingly, a wide variety of regimens may be used to administer fibroblasts and/or EPCs. In one embodiment the disclosure, methods employ isolated mammalian endothelial progenitor cells and the method comprises the steps of: (i) isolating a mammalian cellular population; (ii) enriching for a subpopulation of the cells of step (i), which subpopulation expresses a CD45$^-$ phenotypic profile; (iii) enriching for a subpopulation of the CD45$^-$ cells derived from step (ii) which express a CD34+phenotypic profile; and (iv) isolating the subpopulation of CD34+ cells derived from step (iii) that express a CD31$^{lo/-}$ phenotypic profile, to thereby isolate the endothelial progenitor cells; the order of steps of this method may be variable. The endothelial progenitor cells may be used in an allogeneic manner for administration (including at least intraportal), before, and/or concurrent and/or subsequent to an islet transplant. In another aspect, there is provided a method of isolating mammalian endothelial progenitor cells, to be used with islet transplant, the method comprising the sequential steps of: (i) isolating a mammalian cellular population; (ii) enriching for a subpopulation of the cells of step (i), which subpopulation expresses a CD45$^-$ phenotypic profile; (iii) enriching for a subpopulation of the CD45$^-$ cells derived from step (ii) that express a CD34$^+$ phenotypic profile; and (iv) isolating the subpopulation of CD34+ cells derived from step (iii) that express a CD31$^{lo/-}$ phenotypic profile, to thereby isolate the endothelial progenitor cells.

IV. Fibroblasts

Fibroblasts are utilized herein to enhance tolerance of allogeneic cells for engraftment, including into a hepatic location. The fibroblasts may or may not be allogeneic with respect to the individual receiving or that will receive the engraftment. The fibroblasts may be of any kind. The fibroblasts may or may not be modified prior to their use, such as prior to delivery into the individual. Such modification(s) may be of any kind, including modified to express one or more markers that were not expressed by the fibroblasts as a starting population, for example.

The fibroblast cells may be capable of differentiation into the chondrocytic lineage. They may or may not expresses one or more markers selected from the group consisting of a) NANOG; b) OCT-4; c) SSEA-4; d) stem cell factor receptor; and e) a combination thereof. In specific cases, the fibroblasts may be isolated by a method comprising the steps of: (i) isolating a mammalian cellular population; (ii) enriching for a subpopulation of the cells of step (i), which subpopulation expresses a $CD45^-$ phenotypic profile; and (a) enriching for a subpopulation of the $CD45^-$ cells derived from step (ii) which express a $CD34^+$ phenotypic profile and isolating the subpopulation of said $CD34^+$ cells to thereby isolate fibroblast cells with regenerative properties. The fibroblast cells may be derived from a group of tissue sources selected from: a) foreskin; b) tummy tucks; c) placenta; d) ear lobe; e) adipose tissue; f) omentum; and/or g) Wharton's jelly. In particular embodiments, placental fibroblast cells are utilized, and they may be derived from the fetal side of the placenta. In specific aspects, CD45-negative fibroblasts are utilized that are fetally-derived. The fibroblast cells may be purified for expression of markers of regenerative potential using methods selected from; a) magnetic activated cell sorting; b) flow cytometry sorting; c) cellular panning; d) an affinity-based means to selectively select cells of regenerative potential; and/or e) a size-based means to select for cells possessing regenerative potential.

In some embodiments of the disclosure, fibroblast cells are selected for placental expression of OCT-4. In other embodiments, OCT-4 expression is used as a means of identifying cells for culture and expansion subsequent to exposure to various culture conditions. Oct-4 (oct-3 in humans) is a transcription factor expressed in the pregastrulation embryo, early cleavage stage embryo, cells of the inner cell mass of the blastocyst, and embryonic carcinoma ("EC") cells (Nichols, J. et al. (1998) Cell 95: 379-91), and is down-regulated when cells are induced to differentiate. The oct-4 gene (oct-3 in humans) is transcribed into at least two splice variants in humans, oct-3A and oct-3B. The oct-3B splice variant is found in many differentiated cells whereas the oct-3A splice variant (also previously designated oct-3/4) is reported to be specific for the undifferentiated embryonic stem cell. See Shimozaki et al. (2003) Development 130: 2505-12. Expression of oct-3/4 plays an important role in determining early steps in embryogenesis and differentiation. Oct-3/4, in combination with rox-1, causes transcriptional activation of the Zn-finger protein rex-1, which is also required for maintaining ES cells in an undifferentiated state (Rosfjord, E. and Rizzino, A. (1997) Biochem Biophys Res Commun 203: 1795-802; Ben-Shushan, E. et al. (1998) Mol Cell Biol 18: 1866-78).

The dose of fibroblasts appropriate to be used in accordance with various embodiments of the disclosure will depend on numerous factors. It may vary considerably for different circumstances. The parameters that will determine optimal doses of placental fibroblasts to be administered for primary and adjunctive therapy generally will include some or all of the following: the disease being treated and its stage; the species of the subject, their health, gender, age, weight, and metabolic rate; the subject's immunocompetence; other therapies being administered; and expected potential complications from the subject's history or genotype. The parameters may also include: whether the placental fibroblasts are syngeneic, autologous, allogeneic, or xenogeneic; their potency (specific activity); the site and/or distribution that must be targeted for the fibroblasts to be effective; and such characteristics of the site such as accessibility to fibroblasts and/or engraftment of fibroblasts. Additional parameters include co-administration with fibroblasts of other factors (such as growth factors and cytokines). The optimal dose in a given situation also will take into consideration the way in which the cells are formulated, the way they are administered, and the degree to which the cells will be localized at the target sites following administration. Finally, the determination of optimal dosing necessarily will provide an effective dose that is neither below the threshold of maximal beneficial effect nor above the threshold where the deleterious effects associated with the dose of fibroblasts outweighs the advantages of the increased dose.

The optimal dose of fibroblasts (placental, in some cases) for some embodiments will be in the range of doses used for autologous, mononuclear bone marrow transplantation. For fairly pure preparations of placental fibroblasts, optimal doses in various embodiments will range from $10^4$ to $10^8$ placental fibroblasts cells/kg of recipient mass per administration. In some embodiments the optimal dose per administration will be between $10^5$ to $10^7$ placental fibroblasts cells/kg. In many embodiments the optimal dose per administration will be $5 \times 10^5$ to $5 \times 10^6$ placental fibroblasts cells/kg. By way of reference, higher doses in the foregoing are analogous to the doses of nucleated cells used in autologous mononuclear bone marrow transplantation. Some of the lower doses are analogous to the number of $CD34^+$ cells/kg used in autologous mononuclear bone marrow transplantation.

In a specific embodiment, the fibroblasts are isolated so as to possess substantial homogeneity and in particular embodiments are of fetal origin.

Differentiation is the process by which an unspecialized ("uncommitted") or less specialized cell acquires the features of a specialized cell, such as a nerve cell or a muscle cell, for example. A differentiated cell is one that has taken on a more specialized ("committed") position within the lineage of a cell. The term committed, when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. De-differentiation refers to the process by which a cell reverts to a less specialized (or committed) position within the lineage of a cell. As used herein, the lineage of a cell defines the heredity of the cell, i.e. which cells it came from and what cells it can give rise to. The lineage of a cell places the cell within a hereditary scheme of development and differentiation.

Within the context of the current disclosure, fibroblast cells of fetal origin are extracted or isolated such that they possess placental therapeutic efficacy, in part by selecting of stem cells that are primarily of fetal tissue origin.

As used herein, the phrase differentiates into a mesodermal, ectodermal or endodermal lineage refers to a cell that becomes committed to a specific mesodermal, ectodermal or endodermal lineage, respectively. Examples of cells that differentiate into a mesodermal lineage or give rise to specific mesodermal cells include, but are not limited to, cells that are adipogenic, chondrogenic, cardiogenic, dermatogenic, hematopoetic, hemangiogenic, myogenic, nephrogenic, urogenitogenic, osteogenic, pericardiogenic, or stromal. Examples of cells that differentiate into ectodermal lineage include, but are not limited to epidermal cells, neurogenic cells, and neurogliagenic cells. Examples of cells that differentiate into endodermal lineage include, but are not limited to, pleurigenic cells, hepatogenic cells, cells that give rise to the lining of the intestine, and cells that give rise to pancreogenic and splanchogenic cells.

V. Obtaining, Production and/or Manipulation of Cells

In a particular embodiment, cells are isolated from tissues and/or organs prior to manipulation and/or use; the cells may be fibroblasts, EPCs, or insulin-producing cells, such as islet cells. In specific cases, the isolation procedure utilizes an enzymatic digestion process. Enzymes are used to dissociate tissue to extract cellular populations that are subsequently harvested and grown for isolation of fetal derived fibroblast cells. Many enzymes are known in the art to be useful for the isolation of individual cells from complex tissue matrices to facilitate growth in culture. A broad range of digestive enzymes for use in cell isolation from tissue is available to the skilled artisan ranging from weakly digestive (e.g. deoxyribonucleases and the neutral protease, dispase) to strongly digestive (e.g. papain and trypsin), and such enzymes are available commercially. A non-exhaustive list of enzymes compatible herewith includes mucolytic enzyme activities, metalloproteases, neutral proteases, serine proteases (such as trypsin, chymotrypsin, or elastase), and deoxyribonucleases. In particular cases are enzyme activities selected from metalloproteases, neutral proteases and mucolytic activities. For example, collagenases are known to be useful for isolating various cells from tissues. Deoxyribonucleases can digest single-stranded DNA and can minimize cell-clumping during isolation. Enzymes can be used alone or in combination. Serine protease are preferably used in a sequence following the use of other enzymes as they may degrade the other enzymes being used. The temperature and time of contact with serine proteases must be monitored. Serine proteases may be inhibited with alpha 2 microglobulin in serum and therefore the medium used for digestion is preferably serum-free. EDTA and DNase are commonly used and may improve yields or efficiencies. Preferred methods involve enzymatic treatment with for example collagenase and dispase, or collagenase, dispase, and hyaluronidase, and such methods are provided wherein in certain preferred embodiments, a mixture of collagenase and the neutral protease dispase are used in the dissociating step. More preferred are those methods which employ digestion in the presence of at least one collagenase from *Clostridium histolyticum*, and either of the protease activities, dispase and thermolysin. Still more preferred are methods employing digestion with both collagenase and dispase enzyme activities. Also preferred are methods which include digestion with a hyaluronidase activity in addition to collagenase and dispase activities. The skilled artisan will appreciate that many such enzyme treatments are known in the art for isolating cells from various tissue sources. For example, the LIBERASE BLENDZYME (Roche) series of enzyme combinations of collagenase and neutral protease are very useful and may be used in the instant methods. Other sources of enzymes are known, and the skilled artisan may also obtain such enzymes directly from their natural sources. The skilled artisan is also well-equipped to assess new, or additional enzymes or enzyme combinations for their utility in isolating the cells of the invention. Particular enzyme treatments are 0.5, 1, 1.5, or 2 hours long or longer. In other preferred embodiments, the tissue is incubated at 37° C. during the enzyme treatment of the dissociation step. Diluting the digest may also improve yields of cells as cells may be trapped within a viscous digest.

While the use of enzyme activities may be employed, it is not required for isolation methods as provided herein. Methods based on mechanical separation alone may be successful in isolating the instant cells from the umbilicus as discussed above.

The cells can be re-suspended after the tissue is dissociated into any culture medium as discussed herein above. Cells may be re-suspended following a centrifugation step to separate out the cells from tissue or other debris, for examole. Re-suspension may involve mechanical methods of re-suspending and/or simply the addition of culture medium to the cells.

Providing suitable growth conditions allows for a wide range of options as to culture medium, supplements, atmospheric conditions, and relative humidity for the cells. A particular temperature is 37° C., however the temperature may range from about 35° C. to 39° C. depending on the other culture conditions and desired use of the cells or culture.

In some embodiments there are methods that provide cells that require no exogenous growth factors, except as are available in a supplemental serum provided with a growth medium. Also provided herein are methods of deriving umbilical cells capable of expansion in the absence of particular growth factors. The methods are similar to the method above, however they require that the particular growth factors (for which the cells have no requirement) be absent in the culture medium in which the cells are ultimately re-suspended and grown in. In this sense, the method is selective for those cells capable of division in the absence of the particular growth factors. Particular cells in some embodiments are capable of growth and expansion in chemically-defined growth media with no serum added. In such cases, the cells may require certain growth factors, which can be added to the medium to support and sustain the cells. Particular factors to be added for growth on or in serum-free media include one or more of FGF, EGF, IGF, and PDGF. In more particular embodiments, two, three or all four of the factors are add to serum free or chemically defined media. In other embodiments, LIF is added to serum-free medium to support or improve growth of the cells.

Also provided are methods wherein the cells can expand in the presence of from about 5% to about 20% oxygen in their atmosphere. Methods to obtain cells that require L-valine require that cells be cultured in the presence of L-valine. After a cell is obtained, its need for L-valine can be tested and confirmed by growing on D-valine containing medium that lacks the L-isomer.

Methods are provided wherein the cells can undergo at least 25, 30, 35, or 40 doublings prior to reaching a senescent state. Methods for deriving cells capable of doubling to reach $10^{14}$ cells or more are provided. Particular are those methods that derive cells that can double sufficiently to produce at least about $10^{14}$, $10^{15}$, $10^{16}$, or $10^{17}$ or more cells when seeded at from about $10^3$ to about $10^6$ cells/cm$^2$ in culture. Particularly, these cell numbers are produced within 80, 70, or 60 days or less. In one embodiment, tissue fibroblast cells are isolated and expanded, and possess one or more markers selected from the group consisting of CD10, CD13, CD44, CD73, CD90, CD141, PDGFr-alpha, HLA-A,B,C, and a combination thereof. In addition, the cells may or may not produce one or more of CD31, CD45, CD117, CD141, or HLA-DR, DP, DQ, in specific cases.

VI. Pancreatic Islet Cells

In order to assist the practitioner in the methods of the disclosure, methods of isolating pancreatic islet cells are transplantation are provided and incorporated by reference. In one embodiment, the methodology described in U.S. Patent Application US2006/0182722 are provided: Pancreases can be obtained from male or female donors and techniques developed for combined liver and pancreaticoduodenal procurement (Marsh et al., Surg. Gynecol. Obstet. 1989; 168:254-258). Donors typically range in age from 15 to 50 years old. General exclusion criteria include, for example, systemic bacterial infections, viruses such as human immunodeficiency virus (HIV), human T-cell lymphotrophic virus (HTLV), hepatitis B virus, or hepatitis C virus (HCV), a history of diabetes, extracranial tumors, and risk factors for AIDS. Donor pancreases can be preserved using the two-layer pancreas preservation method, which improves pancreatic tissue adenosine triphosphate (ATP) content, increases the yield of islets isolated from a stored pancreas, allows use of marginal donor pancreases for islet isolation and transplantation, improves the islet isolation success rate, and preserves the integrity of the isolated islets (e.g., such that isolated islets can reverse diabetes). In general, cold University of Wisconsin (UW) Solution (ViaSpan®, DuPont Pharma, Wilmington, Del.) (see U.S. Pat. Nos. 4,798,824 and 4,879,283) or modified UW solution can be poured on top of an equal volume of cold perfluorodecalin (FluoroMed, L. P., Round Rock, Tex.). Typically, the two-layer preservation method is performed in an organ shipping container, which has, for example, a removable lid with a stainless steel mesh plate attached thereto, and inlet and outlet ports. See, for example, the organ shipping container of U.S. Pat. No. 6,490,880. Two layers are formed after adding ViaSpan® or modified-UW solution to the perfluorodecalin as the specific gravity of perfluorodecalin is greater than ViaSpan®. and modified-UW solution. Modified UW solution includes 0.35 to 0.45 g/L potassium hydroxide, 3.00 to 4.00 g/L monosodium phosphate monohydrate, 0.05 to 1.00 g/L calcium chloride dihydrate, 1.10 to 1.30 g/L magnesium sulfate heptahydrate, 33.00 to 38.00 g/L lactobionic acid, 4.00 to 5.00 g/L L-histidine, 15.00 to 20.00 g/L raffinose, 4.00 to 5.00 g/L sodium hydroxide, 15.00 to 25.00 g/L penta starch, 1.00 to 1.50 g/L adenosine, and 0.75 to 1.50 g/L glutathione. In particular, the modified UW solution can include 0.39 g/L potassium hydroxide, 3.45 g/L monosodium phosphate monohydrate, 0.074 g/L calcium chloride dihydrate, 1.23 g/L magnesium sulfate heptahydrate, 35.83 g/L lactobionic acid, 4.66 g/L L-histidine, 17.84 g/L raffinose, 4.60 g/L sodium hydroxide, 20.00 g/L penta starch, 1.34 g/L adenosine, and 0.92 g/L glutathione. Typically, the perfluorodecalin is oxygenated for 30-70 minutes (e.g., 40-60 minutes). For example, medical grade oxygen can be filtered through a 0.2 mm filter (Gelman Sciences, Ann Arbor, Mich.) and the inlet port of the shipping container at a rate of 2.5 L/min. Preferably, the cold storage time of the donor pancreas is less than 12 hours (e.g., less than 10, 8, 6, 4, or 2 hours). Upon receipt of a donor pancreas, integrity of the shipping container can be verified by visual inspection. The pancreas can be removed and rinsed with cold transport solution containing 8.00 to 10.00 g/L mannitol, 3.00 to 6.00 g/L L-histidine, 18.00 to 21.00 g/L gluconic acid, 0.50 to 2.00 g/L potassium hydroxide, 0.01 to 0.05 g/L calcium chloride, 0.50 to 2.00 g/L magnesium sulfate, 0.40 to 0.80 g/L nicotinamide, 0.30 to 0.70 g/L pyruvate, and 1.50 to 3.50 g/L potassium phosphate monobasic. For example cold transport solution can include 8.50 to 9.50 g/L (e.g., 9.11 g/L) D-mannitol, 4.00 to 5.00 g/L (e.g., 4.67 g/L) L-histidine, 18.50 to 20.50 g/L (e.g., 19.63 g/L) D-gluconic acid sodium salt, 0.80 to 1.40 g/L (e.g., 1.12 g/L) potassium hydroxide, 0.025 to 0.045 g/L (e.g., 0.037 g/L) calcium chloride dihydrate, 1.00 to 1.50 g/L (e.g., 1.23 g/L) magnesium sulfate heptahydrate, 0.55 to 0.65 g/L (e.g., 0.61 g/L) nicotinamide, 0.50 to 0.60 g/L (e.g., 0.55 g/L) sodium pyruvate, and 2.50 to 3.25 g/L (e.g., 2.72 g/L) potassium phosphate monobasic. Islets can be isolated from the donor pancreas using an automated method of pancreatic tissue dissociation. See, for example, Ricordi et al., Diabetes 1988; 37:413-420. This method includes the general steps of 1) dissection; 2) distension; 3) dissociation; and 4) collection. Dissection of the pancreas can include removing extraneous fat (while retaining some fat to minimize leaking during distension), and non-pancreatic tissue. Typically, about 80% to about 95% of the fat is removed. The dissected pancreas can be incubated in a topical antibiotic solution containing, for example, gentamicin (Elkins-Sinn, Inc.), Cefazolin (SmithKline Beecham Pharmaceutical), and amphotericin-B (Apothecon®) in cold transport solution, then can be serially rinsed in phenol red-free Hanks' Balanced Salt Solution (Mediatech, Inc., Herndon, Va.). The pancreas can be divided at the neck into the 'body and tail' and 'head' and the following steps performed on each part. In general, the pancreatic duct can be cannulated with an angiocatheter (16-20 gauge) and the pancreas perfused under controlled conditions, including an initial pressure of 80 mmHg followed by an increase in pressure to 180 mmHg for the remainder of the distension procedure. Phase I solution can be used to perfuse the pancreas. Phase I solution includes 5.00 to 6.00 g/L mannitol, 0.50 to 0.70 g/L sodium hydroxide, 5.00 to 7.00 g/L sodium chloride, 0.25 to 0.40 g/L potassium hydroxide, 0.05 to 0.15 g/L calcium chloride, 0.15 to 0.25 g/L magnesium sulfate, and 3.00 to 4.00 g/L sodium phosphate monobasic. For example, Phase I solution can include 5.47 g/L D-mannitol, 0.60 g/L sodium hydroxide, 6.14 g/L sodium chloride, 0.33 g/L potassium hydroxide, 0.11 g/L calcium chloride dihydrate, 0.20 g/L magnesium sulfate heptahydrate, and 3.45 g/L sodium phosphate monobasic. Typically, the Phase I solution contains 1,000 to 3,600 Wunsch units (collagenase activity) or 28,000 to 128,500 caseinase units (proteolytic activity) of collagenase. For example, the Phase I solution can include 1500 to 3000 (e.g., 1,562 to 2,954 or 2,082 to 2,363) Wunsch units, or 42,000 to 108,000 (e.g., 42,328 to 107,064 or 56,437 to 85,651) caseinase units of collagenase. A suitable collagenase includes Liberase™HI (Roche Molecular Biochemicals, Indianapolis, Ind.), which has been specifically formulated for human islet isolation procedures. See, Linetsky et al., Diabetes 1997; 46:1120-1123. Preferably, powdered Liberase™HI is reconstituted at least 20 minutes before, but less than 2 hours before, addition to the Phase I solution. The Phase I solution also can include a protease inhibitor (e.g., a trypsin inhibitor such as 4-(2-aminoethyl)-benzenesulfonyl fluoride hydrochloride (Pefabloc® SC PLUS), TLCK (1-Chloro-3-tosylamido-7-amino-2-heptanone HCl), or trypsin inhibitor from soybean). For example, the Phase I solution can include 0.05 to 0.15 mg/mL of Pefabloc® SC PLUS, which specifically inhibits endogenous proteases and decreases auto-digestion. The Phase I solution also can include 8 to 12 units/mL of heparin (e.g., Monoparin®, Accurate Chemical and Scientific Corporation). For example, the Phase I solution can include 10 units/mL of heparin.

In some embodiments, the Phase I solution contains 1,000 to 3,600 Wunsch units of collagenase, 0.05 to 0.15 mg/mL of a trypsin inhibitor, and 10 units/mL of heparin. After a sufficient period of time of cold perfusion, e.g., 8-20 minutes, the distended pancreas can be further trimmed of remaining capsule and placed into a dissociation chamber (e.g., a sterile stainless steel chamber (Wahoff et al., Ann. Surg. 1995; 222:562-579), also known as a Ricordi chamber). Collagenase that "leaked" from the distended pancreas can be added to the chamber. Typically, the Ricordi chamber is in a circulation system that includes a heat exchange coil (e.g., a stainless steel coil), a pump, a temperature monitor and sensor, a loading flask, a fluid collection flask, a sample collecting flask, and tubes for fluidly connecting components. Flow direction can be controlled using, for example, valves or clamps. The heat exchange coil can be placed in a water bath. In one embodiment of a circulation system that contains a Ricordi chamber, there are a stainless steel coil for heat exchange, six (6) tubes with small diameter (Master Flex tubing, size 16), four (4) tubes with large diameter (Master Flex tubing, size 17), steel 3-way stopcock for sampling, four (4) plastic clamps, 250 mL conical tube, tri-pour graduated disposable beaker, 1000 mL, bell-shaped plastic cover, two (2) T-connectors, (1) T-connector with luer lock port, and one (1) Y-connector, 18 inch steel ring stand with two arms, Ismatec pump, Mon-a-therm temperature monitor and sensor, and water bath. The system can be filled with Phase I solution and air evacuated to begin the digestion phase. In particular, Phase I solution can be allowed to flow from the loading flask through the pump, heat exchange coil, and Ricordi chamber to the fluid collecting flask. After 10% to 30% of the volume of Phase I solution reaches the fluid collecting flask, the flow of the system can be adjusted such that the Phase I solution is recirculated through the system, i.e., the Phase I solution flows from the fluid collecting flask to the chamber and from the chamber to the fluid collecting flask. The chamber can be agitated while the fluid is being recirculated to aid tissue dissociation. Temperature of the fluid can be maintained at 25° C. to 37° C. The collection phase can begin once there is an increase in the amount of tissue liberated from the chamber, most or all of the islets are free of the surrounding acinar tissue, intact islets are observed, and the acinar tissue becomes finer (small cell clusters). Diphenylthiocarbazone (DTZ) staining can be used to distinguish islets from non-islet tissue. See, Latif et al., Transplantation 1988; 45:827-830. DTZ selectively binds to the zinc-insulin complex in islet beta cell granules, and results in a red staining of the islets. DTZ staining provides a rapid means for discrimination of islet from acinar tissue, and the positive reaction indicates that insulin-containing beta cells are present. During the collection phase, temperature of the system can be reduced to about 10° C. to about 30° C. Fluid in the fluid collecting flask can be allowed to flow through the pump and heat exchange coil into the Ricordi chamber, and Phase II solution (RPMI 1640, catalog #99-595-CM, Mediatech, Inc., Herndon, Va.) can be added to a loading flask. The Phase II solution can be pumped through the circulation system to dilute the collagenase and to wash the tissue. Digested material can be collected in flasks containing Phase II solution and human serum albumin (HSA), and the collected material washed two to five times using cold storage solution. Cold storage solution can include 16.00 to 20.00 g/L raffinose, 4.00 to 6.00 g/L histidine, 4.00 to 5.00 g/L sodium hydroxide, 30.00 to 40.00 g/L lactobionic acid, 0.30 to 0.50 g/L potassium hydroxide, 0.05 to 0.10 g/L calcium chloride, 1.00 to 1.50 g/L magnesium sulfate, 3.00 to 4.00 g/L sodium phosphate monobasic, 19.00 to 21.00 g/L pentastarch, 8.00 to 12.00 U/mL heparin, and 8.00 to 12.00 .mu.g/mL insulin. For example, cold storage solution can include 17.84 g/L D (+) raffinose, 4.66 g/L L-histidine, 4.60 g/L sodium hydroxide, 35.83 g/L lactobionic acid, 0.39 g/L potassium hydroxide, 0.39 g/L calcium chloride dihydrate, 1.23 g/L magnesium sulfate heptahydrate, 3.45 g/L sodium phosphate monobasic, 2% penta starch, 10 U/mL heparin, and 10 .mu.g/mL insulin. Cold storage solution can be made by combining H-Phase II solution (80% by volume) with 10% penta starch (i.e., 100 g/L) (20% by volume), and adding 8.00 to 12.00 U/mL heparin, and 8.00 to 12.00 .mu.g/mL insulin. H-Phase II solution can include 16.00 to 20.00 g/L raffinose, 4.00 to 6.00 g/L histidine, 4.00 to 5.00 g/L sodium hydroxide, 30.00 to 40.00 g/L lactobionic acid, 0.30 to 0.50 g/L potassium hydroxide, 0.05 to 0.10 g/L calcium chloride, 1.00 to 1.50 g/L magnesium sulfate, and 3.00 to 4.00 g/L sodium phosphate monobasic. The pH of H-Phase II solution can be adjusted to a pH of 7.3-7.5 using hydrochloric acid or sodium hydroxide. Density of H-Phase II solution typically is 1.063.+-0.0.003. For example, H-Phase II solution can include 17.84 g/L D (+) raffinose, 4.66 g/L L-histidine, 4.60 g/L sodium hydroxide, 35.83 g/L lactobionic acid, 0.39 g/L potassium hydroxide, 0.39 g/L calcium chloride dihydrate, 1.23 g/L magnesium sulfate heptahydrate, and 3.45 g/L sodium phosphate monobasic. The washed tissue can be resuspended in capping layer solution and HSA (e.g., 25% HSA). Capping layer solution can include 16.00 to 20.00 g/L raffinose; 4.00 to 6.00 g/L histidine; 4.00 to 5.00 g/L sodium hydroxide; 30.00 to 40.00 g/L lactobionic acid; 0.30 to 0.50 g/L potassium hydroxide; 0.05 to 0.10 g/L calcium chloride; 1.00 to 1.50 g/L magnesium sulfate; 3.00 to 4.00 g/L sodium phosphate monobasic; and 19.00 to 21.00 g/L pentastarch. For example, capping layer solution can have a density of 1.035 to 1.036 g/cm$^3$ and can include 17.84 g/L D (+) raffinose, 4.67 g/L L-Histidine, 4.6 g/L sodium hydroxide, 35.83 g/L lactobionic acid, 0.393 g/L potassium hydroxide, 0.07 g/L calcium chloride dihydrate, 1.23 g/L magnesium sulfate heptahydrate, 3.45 g/L sodium phosphate monobasic, and 2% penta starch. Capping layer solution can be made by combining H-Phase II solution (80% by volume) with 10% penta starch (i.e., 100 g/L) (20% by volume). Islets can be purified using continuous density gradient separation. Gradients can be prepared using iodixanol (OptiPrep™, Nycomed, Roskilde, Denmark) (density 1.32 g/cm.sup.3) and capping layer solution, cold storage solution, and/or high-density (HD) stock solution. HD stock solution can include 16.00 to 20.00 g/L raffinose; 4.00 to 6.00 g/L histidine; 4.00 to 5.00 g/L sodium hydroxide; 30.00 to 40.00 g/L lactobionic acid; 0.30 to 0.50 g/L potassium hydroxide; 0.05 to 0.10 g/L calcium chloride; 1.00 to 1.50 g/L magnesium sulfate; 3.00 to 4.00 g/L sodium phosphate monobasic; 15.00 to 25.00 g/L pentastarch; and 200 to 300 ml/L iodixanol. The density of the HD stock solution typically is 1.112.+-0.0.003 g/cm.sup.3. For example, HD stock solution can include 17.84 g/L D (+) raffinose, 4.67 g/L L-Histidine, 4.6 g/L sodium hydroxide, 35.83 g/L lactobionic acid, 0.39 g/L potassium hydroxide, 0.07 g/L calcium chloride dihydrate, 1.23 g/L magnesium sulfate heptahydrate, 3.45 g/L sodium phosphate monobasic, 20 g/L penta starch, and 250 mL/L iodixanol (Optiprep™). In some embodiments, HD stock solution also can include 8.00 to 12.00 U/mL of heparin and/or 8.00 to 12.00 .mu.g/mL insulin. A bottom density gradient solution having a density that ranges from 1.08 to 1.13 g/cm$^3$ can be prepared by mixing HD stock solution and cold storage solution. A light density gradient solution having a density of 1.050 to 1.080 g/cm.sup.3 can be made by mixing iodixanol and cold storage solution, while a heavy density gradient solution having a density of 1.06 to 1.13 g/cm$^3$ can be made by mixing cold storage solution and HD stock solution.

A continuous gradient can be made, for example, in a dual chamber gradient maker, by combining the light and heavy density gradient solutions. The bottom density gradient can be transferred to a cell processing bag for a cell separator such as the Cobe 2991 cell separator (Lakewood, Colo.), and the continuous gradient can be overlaid on the bottom density gradient. The resuspended tissue (as described above) can be placed on the continuous gradient followed by a capping layer solution then the gradient can be spun to separate the islets. Fractions can be collected and assayed for the presence of islets as described below. Fractions with islet purities (percentage of DTZ positive cells) >10% can be combined for culture. Purified islets can be cultured using a chemically defined culture medium that is effective for maintaining viability of human pancreatic islets under culture conditions. Typically, islets are cultured at a temperature of 22° C. or 37° C. and an atmosphere of 95% air and 5% $CO_2$. In some embodiments, islets can be cultured in an atmosphere of room air. Viability of islets can be assessed using trypan blue or a fluorescent dye inclusion/exclusion assay. See, for example, Barnett et al., Cell Transplant. 2004; 13(5):481-8. The chemically defined culture medium can include one or more of the following: insulin, zinc sulfate, selenium, transferrin, sodium pyruvate, HEPES (N-[2-Hydroxyethyl]piperazine-N'[2-ethanesulfonic acid]), HSA, and heparin. For example, the chemically defined culture medium can include 5.50 to 7.50 .mu.g/mL insulin, 15 to 18 .mu.M zinc sulfate, 5.50 to 7.50 ng/mL selenium (e.g., selenous acid), and 5.50 to 7.50 .mu.g/mL transferrin (e.g., human transferrin). Such a culture medium further can include one or more of the following: 3 to 7 mM sodium pyruvate, 20 to 30 mM HEPES, 0.50 to 1.50 mg/mL HSA, 8.00 to 12.00 U/mL of heparin, 1 to 3 mM L-Alynyl-L-glutamine, and 4.50 to 6.50 .mu.g/mL linoleic acid. Typically, when the cells are to be cultured under 95% room air and 5% CO.sub.2, the chemically defined culture medium includes bicarbonate (e.g., 1.75 to 2.75 g/L such as 2.2 g/L). The bicarbonate concentration can be reduced if the cells are cultured in 100% room air. In some embodiments, the chemically defined culture medium also includes an antibiotic such as ciprofloxacin (Bayer Corporation). In one embodiment, a chemically defined culture medium can be CMRL 1066 (Mediatech, Inc., Herndon, Va.) supplemented with 25 mM HEPES, 2 mM L-Alynyl-L-Glutamine, 5 mM sodium pyruvate, 1% (vol/vol), ITS additive (6.25 .mu.gg/mL human recombinant insulin, 6.25 μg/mL human transferrin, 6.25 ng/mL selenous acid, 1.25 mg/mL HSA, 5.35 μg/mL linoleic acid), 16.7 μM zinc sulfate, 20 μg/mL ciprofloxacin (Bayer Corporation) and 0.5% final concentration of 25% HSA. Human Insulin-like Growth Factor-I (IGF-I, GRO PEP Pty Ltd, Adelaide, South Australia) can be added to the islet culture. For example, 90 to 110 ng/mL (e.g., 100 ng/mL) of IGF-1 can be added to the culture. Typically, the islets are cultured overnight at 37° C. then for an additional 1 to 3 days at 22° C. Pretransplant culture of islets can provide beneficial metabolic and immunologic effects. For example, culturing islets for two days can improve the metabolic efficacy of the cultured islets relative to freshly isolated islets. Pretransplant islet culture also can allow time for T-cell-directed immunosuppression to be achieved in the recipient before the transplant. Without being bound to a particular mechanism, achieving T-cell-directed immunosuppression may reduce islet-directed immune responses mediated by autoreactive, primed T cells to which the transplanted islets are immediately exposed. As described herein, delaying transplantation until two days after the initiation of therapy with T-cell-depleting antibodies prevents exposure of transplanted islets to the cytokine release associated, to varying degrees, with the first and second antibody infusions. Furthermore, pretransplant culture of islets allows quality control studies to be performed before the infusion of tissue.

Purified islet cells can be cryopreserved by suspending the cells in a cryopreservative such as dimethylsulfoxide (DMSO) or ethylene glycol, or a mixture of cryopreservatives. See, for example, Miyamoto et al., Cell Transplant 2001; 10(4-5):363-71; Evans et al., Transplantation 1990;

50(2):202-206; and Lakey et al., Cell Transplant 1996; 5(3):395-404. Islet cells can be cryopreserved after purification or culture. Typically, the cryopreservative is added in a stepwise fashion and the islets are slow cooled to –40° C. then stored at –196° C. Islets can be rapidly thawed (e.g., in a 37° C. water bath) and assayed before use. Cryopreservation can allow for long-term storage of these cells for later transplantation or other purpose. Cryopreserving collections of purified populations of islets cells is particularly useful for producing an islet bank.

Preparations of isogenic islet cells purified using the methods described herein typically result in successful transplants in at least 55% (e.g., at least 60%, 65%, 70%, 75%, 80%, 85%, 90%, or 95%) of the patients. A transplant is considered a success when a patient sustains insulin independence, nornoglycemia, and freedom from hypoglycemia for at least one year after a single-donor islet transplant.

Preparations of purified islet cells can be assayed to confirm that the islets have sufficient potency to be transplanted. As used herein, "transplant potency" refers to an estimate of the probability that the preparation of islets can be successfully transplanted in a patient and is based on one or more of the following parameters: safety of the islet preparation, islet cell number, cellular composition of islet preparation, number of beta cells, insulin content, tissue volume, viability, ATP content, percent of islet equivalents recovered after cell culture, percent necrotic and apoptotic cells, glucose-stimulated insulin release, and oxygen consumption rate (OCR). For example, transplant potency can be estimated based on the ATP/DNA ratio, OCR/DNA ratio, and beta cell number. Preparations of purified islets that have at least a 60% probability of constituting a successful transplant are particularly useful. Safety of an islet preparation can be determined by assaying for the presence of aerobic and anaerobic organisms and fungi, *mycoplasma*, and other adventitious agents (e.g., viruses) using known techniques. For example, a sample can be Gram stained to detect bacteria. Islet cells suitable for transplantation do not contain detectable organisms and are functionally sterile. Assessing safety also can include measuring endotoxin present in the preparation. Islet cell preparations suitable for transplant have an endotoxin content of 1.7 EU/mL (5 EU/kg recipient body weight) or less. Islet cell number can be assessed by staining with DTZ and quantifying the size distribution of the stained cells using a light microscope with ocular micrometer. See, Ricordi et al., Acta Diabetol. Lat. 1990; 27:185-195. Islet volume can be calculated, based on the assumption that islets are spherical, and the number of islets is expressed in terms of islet equivalents (IE), with one IE equal to a 150 μm diameter islet. Preparations of islets containing at least $2.2 \times 10^5$ IE (e.g., $2.7 \times 10^5$, $3.5 \times 10^5$, $4.5 \times 10^5$, $5.5 \times 10^5$, $7.0 \times 10^5$, $9.0 \times 10^5$, $1.1 \times 10^6$, or $1.4 \times 10^6$ IE) are particularly useful as 5,000 to 20,000 IE can be transplanted/kg recipient body weight. One IE can include from about 600 to about 8600 cells. The cellular composition of islet preparations can be assessed using standard immunoassay methods. Antibodies that have binding affinity for insulin, glucagon, somatostatin, pancreatic polypeptide, amylase, and cytokeratin 19 can be used to identify beta-, alpha-, delta-, pp-, acinar, and ductal cells, respectively. Such antibodies are commercially available, e.g., from DAKO, Carpinteria, Calif. or Sigma Chemical Co., St. Louis, Mo. Binding can be detected by labeling, either directly or indirectly, the antibody having binding affinity for the particular protein (e.g., insulin) or a secondary antibody that binds to such an antibody. Suitable labels include, without limitation, radionuclides (e.g., $^{125}$I, $^{131}$I, $^{35}$S, $^{3}$H $^{32}$P, $^{33}$P or

[14]C), fluorescent moieties (e.g., fluorescein, FITC, PerCP, rhodamine, or PE), luminescent moieties (e.g., Qdot™ nanoparticles supplied by the Quantum Dot Corporation, Palo Alto, Calif.), compounds that absorb light of a defined wavelength, or enzymes (e.g., alkaline phosphatase or horseradish peroxidase). Antibodies can be indirectly labeled by conjugation with biotin then detected with avidin or streptavidin labeled with a molecule described above. Methods of detecting or quantifying a label depend on the nature of the label and are known in the art. Examples of detectors include, without limitation, x-ray film, radioactivity counters, scintillation counters, spectrophotometers, colorimeters, fluorometers, luminometers, and densitometers. Immunological assays can be performed in a variety of known formats, including sandwich assays, competition assays (competitive RIA), or bridge immunoassays. See, for example, U.S. Pat. Nos. 5,296,347; 4,233,402; 4,098,876; and 4,034,074. The number of beta cells can be calculated based on the total DNA content and proportion of beta cells identified in the cellular composition sample. One IE can include from about 145 to 4000 beta cells. Preparations of islet cells that contain at least $1 \times 10^6$ beta cells/kg body weight of recipient (i.e., $4.5 \times 10^7$ beta cells for a 45 kg recipient, $5 \times 10^7$ beta cells for a 50 kg recipient, and $5.5 \times 10^7$ beta cells for a 55 kg recipient) can be used. Preparations containing higher numbers of beta cells (e.g., at least $2 \times 10^6$ beta cells/kg body weight of recipient, at least $3.5 \times 10^6$ beta cells/kg body weight of recipient, or at least $5.0 \times 10^6$ beta cells/kg body weight of recipient) are particularly useful. For example, preparations containing at least $3.5 \times 10^6$ beta cells/kg body weight of recipient (i.e., about $1.58 \times 10^8$ beta cells for a 45 kg recipient, about $1.75 \times 10^8$ beta cells for a 50 kg recipient, and about $1.9 \times 10^8$ beta cells for a 55 kg recipient) can sustain insulin independence for at least one year. Insulin content can be assessed using an immunoassay, e.g., the Human Insulin Enzyme Immunoassay (EIA) kit from Mercodia, Sweden, and corrected for the DNA content. Pico Green can be used to assess DNA content. In the Pico Green method, islet cells can be lysed with a solution containing ammonium hydroxide and a non-ionic detergent. Pico Green can be added to the sample and incubated in the dark. Samples are read on a fluorometer with an excitation of 480 nm and an emission of 520 nm and compared with a standard curve. Typically, one IE can include from about 4 to about 60 ng of DNA. Tissue volume of the preparation refers to the volume of the islet cell pellet before transplant. Islet cells can be collected in a pre-weighed tissue culture flask and the islets can be allowed to sediment to a bottom corner of the flask over a period of time (e.g., 5 minutes). The medium can be removed from the flask and the mass recorded. Suitable preparations of islet cells have a volume of 10 mL or less (e.g., 8 mL or less, 7.0 mL or less, 5 mL or less, 3 mL or less, or 2 mL or less). ATP content of islet cell preparations can be assessed via high performance liquid chromatography (HPLC) or by using an immunoassay (e.g., an ATP Determination Kit from Invitrogen Corp., Carlsbad, Calif.). In either method, samples can be prepared using the methods of Micheli et al. Clin. Chem. Acta 1993, 220:1-17 in which trichloroacetic acid is used to extract the ATP and a freon/amine solution is used to neutralize the sample. Preparations of islet cells that have at least 76 pmol ATP/μg DNA (e.g., at least 80, 90, 100, 110, 150, 175, 190, or 193), as measured by HPLC, are particularly useful for transplants. A fluorescent dye inclusion/exclusion assay can be used to assess viability. See, for example, London et al., Hormone & Metabolic Research—Supplement 1990; 25:82-87. For example, fluorescein diacetate and propidium iodide (PI) can be used to assess viability. Fluorescein diacetate is dissociated by intracellular enzymes into free fluorescein, which fluoresces green under blue light excitation (490 nm) and provides evidence that the cells are alive and metabolically active. If the cell membrane has been damaged, PI can enter into the cell, intercalate into the nuclear DNA, and fluoresce red under green light excitation (545 nm). The proportion of green (viable) and red (dead) cells gives an indication of viability of the islet preparation. Alternatively, SYTO-13/ethidium bromide (SYTO/EB) and calcein AM/ethidium homodimer (C/EthD) fluorescent staining can be used to assess viability. See, for example, Barnett et al., Cell Transplant. 2004; 13(5):481-8. Preparations of islets that contain at least 70% (e.g., at least 75%, 80%, 85%, 90%, 95%, or 97%) viable cells are particularly useful for transplants.

The percent of IE recovered after culture can be determined using DTZ as described above. Preparations of islets in which at least 70% (e.g., least 75%, 80%, 85%, 90%, or 95%) of the IE were recovered after culture are particularly useful for transplants. The percent necrotic and apoptotic cells can be assessed using known methods. For example, apoptosis can be assessed by examining DNA fragmentation. For example, a Cell Death Detection ELISA.sup.Plus (Roche Biochemicals, Indianapolis, Ind.) can be used to detect cytoplasmic histone-associated DNA fragments. Preparations of islets in which 30% or less (e.g., 25%, 20%, 15%, 10%, 5%, or less) of the cells are apoptotic or necrotic are useful for transplants. Glucose-stimulated insulin release is a measure of the functional capacity of the preparation. Standard techniques for static incubation and assessment of insulin release corrected for DNA content are utilized to determine the functional capacity of the islets. Ricordi et al., Acta Diabetol. Lat. 1990; 27:185-195. A stimulation index is calculated by dividing insulin release at 16.7 mM glucose by insulin release at 1.7 mM glucose. Preparations of islets that have a stimulation index of >1 (e.g., >4, >7, >10, >14, >17, or >27) are particularly useful for transplants. OCR can be measured using an OCR chamber (e.g., from Instech Laboratories, Inc., Plymouth Meeting, Pa.). See, for example, Papas et al., Cell Transplant. 2003; 12: 177; Papas et al., Cell Transplant. 2003; 12: 176; and Papas et al., Cell Transplant. 2001; 10: 519. Preparations of islets having an OCR of greater than >75 nmol/min/mg DNA (e.g., greater than >100, >150, >200, or >230 nmol/min/mg DNA) are particularly useful for transplants. Islet cells can be transplanted into, for example, the portal vein of a patient using surgical techniques such as minilaparotomy or percutaneous transhepatic portal venous catheterization. Prior to transplant, patients can undergo induction immunosuppression using different therapy regimens. Patients also can undergo post-transplant immunosuppression regimens. For example, induction therapy can include treatment with rabbit antithymocyte globulin (RATG), daclizumab, and etanercept (i.e., soluble tumor necrosis factor (TNF) receptor). RATG is a potent induction agent and also interferes with leukocyte responses to chemotactic signals and inhibits the expression of integrins required for firm cellular adhesion. Selective inhibition of TNFα in the peritransplant period may be able to promote reversal of diabetes after marginal-mass islet transplants. Post-transplant, the function of engrafted islets may be enhanced by replacing or minimizing tacrolimus at 1 month post-transplant. Another example of an induction therapy can include use of anti-CD3 mAb hOKT3γ1 (Ala-Ala), which can inactivate autoreactive, primed, islet-directed T cells immediately posttransplant. Anti-CD3 mAb, hOKT3γ1 (Ala-Ala), is a humanized antibody that retains the binding region of OKT3 but replaces the murine framework with human amino acids. In addition, the human IgG1 Fc is mutated to prevent binding to the Fc receptor (FcR). Clinically, this engineered antibody has proven effective in preserving residual beta-cell function in new-onset type 1 diabetes. In addition, the hOKT3γ1 (Ala-Ala) reversed kidney graft rejection. This dual activity against both autoreactive and alloreactive T cell responses occurred with markedly fewer side effects, as compared with the parental OKT3 antibody.

In one embodiment of the disclosure, fibroblasts are used to enhance tolerance of allogeneic islets or autologous islets. Fibroblasts may be used in an unmanipulated manner, or manipulated by culture conditions, or may be genetically manipulated. Genetic manipulation may involve augmentation of immune suppressive/immune modulatory aspects, and/or transfection with autoantigen. In the case of diabetes said autoantigen would involve islet autoantigens such as GAD, ISLA-1, insulin, pro-insulin, NRP, or peptides thereof. In one embodiment, fibroblasts are generated according to protocols previously utilized for treatment of patients utilizing bone marrow derived MSC. In some embodiments of the invention transfection is accomplished by use of lentiviral vectors, said means to perform lentiviral mediated transfection are well-known in the art and discussed in the following references [82-88]. Some specific examples of lentiviral based transfection of genes into adherent cells include transfection of SDF-1 to promote stem cell homing [89], or growth factors such as FGF-18 [90, 91], HGF [92], akt [93], TRAIL [94-97], PGE-1 [98], NUR77 to enhance migration [99], BDNF [100], HIF-1 alpha [101], CCL2 [102], interferon beta [103], HLA-G to enhance immune suppressive activity [104], hTERT [105], cytosine deaminase [106], OCT-4 to reduce senescence [107, 108], BAMBI to reduce TGF expression [109], HO-1 for antiapoptosis [110], LIGHT [111], miR-126 to enhance angiogenesis [112, 113], bcl-2 to prevent apoptosis [114], telomerase and myocardin to induce cardiogenesis [115], CXCR4 to accelerate hematopoietic recovery [116] and reduce renal allograft rejection [117], wnt11 [118], Islet-1 to promote pancreatic differentiation [119], IL-27 to reduce autoimmune disease [120], ACE-2 to reduce sepsis [121], CXCR4 to reduce liver failure [122, 123], and the HGF antagonist NK4 to reduce cancer [124].

Cell cultures are tested for sterility weekly, endotoxin by limulus amebocyte lysate test, and *mycoplasma* by DNA-fluorochrome stain.

In order to determine the quality of fibroblast cultures, flow cytometry is performed on all cultures for surface expression of SH-2, SH-3, SH-4 MSC markers and lack of contaminating CD14- and CD-45 positive cells. Cells were detached with 0.05% trypsin-EDTA, washed with DPBS+ 2% bovine albumin, fixed in 1% paraformaldehyde, blocked in 10% serum, incubated separately with primary SH-2, SH-3 and SH-4 antibodies followed by PE-conjugated anti-mouse IgG(H+L) antibody. Confluent fibroblasts in 175 cm² flasks are washed with Tyrode's salt solution, incubated with medium 199 (M199) for 60 min, and detached with 0.05% trypsin-EDTA (Gibco). Cells from 10 flasks were detached at a time and fibroblasts are resuspended in 40 ml of M199+1% human serum albumin (HSA; American Red Cross, Washington DC, USA). Fibroblasts harvested from each 10-flask set were stored for up to 4 h at 4° C. and combined at the end of the harvest. A total of 2-10 ' 10⁶ fibroblasts/kg were resuspended in M199+1% HSA and centrifuged at 460 g for 10 min at 20° C. Cell pellets were resuspended in fresh M199+1% HSA media and centrifuged at 460 g for 10 min at 20° C. for three additional times. Total harvest time was 2-4 h based on MSC yield per flask and the target dose. Harvested fibroblasts are cryopreserved in Cryocyte (Baxter, Deerfield, IL, USA) freezing bags using a rate controlled freezer at a final concentration of 10% DMSO (Research Industries, Salt Lake City, UT, USA) and 5% HSA. On the day of infusion cryopreserved units were thawed at the bedside in a 37° C. water bath and transferred into 60 ml syringes within 5 min and infused intravenously into patients over 10-15 min. Patients are premedicated with 325-650 mg acetaminophen and 12.5-25 mg of diphenhydramine orally. Blood pressure, pulse, respiratory rate, temperature and oxygen saturation are monitored at the time of infusion and every 15 min thereafter for 3 h followed by every 2 h for 6 h.

EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

Enhancement of Glucose Control by Islets Co-Transplanted with Fibroblasts

The beta cell toxic antibiotic streptozocin (STZ) (Sigma-Aldrich St. Lois, MO, USA) was used to induce diabetes in BALB/c mice (65 mg/kg for 5 days). Islets were isolated from C57/BL6 mice with stationary collagenase digestion and Ficoll density purification followed by handpicking. The BALB/c recipients (either sex) were diabetic for 1-3 wk before islet transplantation.

The recipients were anesthetized with Avertin (2,2,2,-tribromoethanol), a flank incision was made, and the left kidney was mobilized. A small incision was made in the upper pole of the kidney, and a pouch was created by separating the capsule from the kidney parenchyma with a fine glass probe toward the lower and anterolateral aspect of the kidney. Freshly isolated and purified islets (>95% purity) were brought to the center of the 10×35-mm petri dish in RPMI-1640 supplemented with 25 mM HEPES, 10% fetal calf serum, and 1% penicillin and streptomycin and then drawn up into a PE-50 catheter (0.76-mm ID, 30 cm long) with an attached micromanipulator syringe. The catheter tip was closed with a hemoclip, and the whole syringe and catheter was spun at 350 rpm for 15-20 s to pellet the islets at the tip. After removal of the hemoclip, the tip was inserted under the kidney capsule, and the islet pellet was slowly advanced into the pouch. The catheter was removed, and the entrance was sealed with an ophthalmic cautery. Transplantation was considered technically successful if the non-fasting blood glucose returned to normal (<9.4 mM) within 2-3 days (10). Islet graft function was evaluated as follows. Mice received either: a) no Streptozocin; b) Streptozocin; c) Streptozocin+bone marrow mesenchymal stem cells (100, 000 cells) (purchased from AllCells) and d) Streptozocin+ Fibroblast selected for CD73 (100,000 cells).

The intraperitoneal glucose tolerance test (IPGTT) was performed 30 days post-transplantation according to previously reported protocols (Angiotensin II type 2 receptor is critical for the development of human fetal pancreatic progenitor cells into islet-like cell clusters and their potential for transplantation. Leung K K, Liang J, Ma M T, Leung P S Stem Cells. 2012 March; 30(3):525-36). In brief, all groups received the intraperitoneal injection of water dissolved glucose (1 g/kg body weight) after 6 h fasting, and the blood glucose was monitored at 50, 100, 150 minutes after the injection of glucose. FIG. 1 demonstrates enhancement of glucose control by islets co-transplanted with fibroblasts, based on blood glucose levels.

REFERENCES

All patents and publications mentioned in the specification are indicative of the level of those skilled in the art to which the invention pertains. All patents and publications are herein incorporated by reference in their entirety to the same extent as if each individual publication was specifically and individually indicated to be incorporated by reference.

PATENTS AND PATENT APPLICATIONS

U.S. Pat. No. 4,034,074
U.S. Pat. No. 4,098,876
U.S. Pat. No. 4,233,402
U.S. Pat. No. 4,798,824
U.S. Pat. No. 4,879,283
U.S. Pat. No. 5,296,347
U.S. Pat. No. 6,490,880
U.S. Patent Application US 2006/0182722

PUBLICATIONS

1. Shapiro, A. M., et al., *International trial of the Edmonton protocol for islet transplantation*. N Engl J Med, 2006. 355(13): p. 1318-30.
2. van der Torren, C. R., et al., *Identification of donor origin and condition of transplanted islets in situ in the liver of a type 1 diabetic recipient*. Cell Transplant, 2016.
3. Zinger, A. and G. Leibowitz, *Islet transplantation in type 1 diabetes: hype, hope and reality—a clinician's perspective*. Diabetes Metab Res Rev, 2014. 30(2): p. 83-7.
4. Vantyghem, M. C., et al., *Treating diabetes with islet transplantation: lessons from the past decade in Lille*. Diabetes Metab, 2014. 40(2): p. 108-19.
5. Quaranta, P., et al., *Co-transplantation of endothelial progenitor cells and pancreatic islets to induce long-lasting normoglycemia in streptozotocin-treated diabetic rats*. PLoS One, 2014. 9(4): p. e94783.
6. Wils, J., J. Favre, and J. Bellien, *Modulating putative endothelial progenitor cells for the treatment of endothelial dysfunction and cardiovascular complications in diabetes*. Pharmacol Ther, 2016.
7. Wu, H., et al., *Diabetes-Induced Oxidative Stress in Endothelial Progenitor Cells May Be Sustained by a Positive Feedback Loop Involving High Mobility Group Box-1*. Oxid Med Cell Longev, 2016. 2016: p. 1943918.
8. He, F., et al., *Increased CD4+CD25+Foxp3+ regulatory T cells in tolerance induced by portal venous injection*. Surgery, 2009. 145(6): p. 663-74.
9. Steinman, R. M., D. Hawiger, and M. C. Nussenzweig, *Tolerogenic dendritic cells*. Annu Rev Immunol, 2003. 21: p. 685-711.

10. Adema, G. J., *Dendritic cells from bench to bedside and back*. Immunol Lett, 2009. 122(2): p. 128-30.
11. Steinman, R. M. and K. Inaba, *Myeloid dendritic cells*. J Leukoc Biol, 1999. 66(2): p. 205-8.
12. Steinman, R. M., *Dendritic cells and the control of immunity: enhancing the efficiency of antigen presentation*. Mt Sinai J Med, 2001. 68(3): p. 160-6.
13. Bonifaz, L., et al., *Efficient targeting of protein antigen to the dendritic cell receptor DEC-205 in the steady state leads to antigen presentation on major histocompatibility complex class I products and peripheral CD8+ T cell tolerance*. J Exp Med, 2002. 196(12): p. 1627-38.
14. Mukhopadhaya, A., et al., *Selective delivery of beta cell antigen to dendritic cells in vivo leads to deletion and tolerance of autoreactive CD8+ T cells in NOD mice*. Proc Natl Acad Sci USA, 2008. 105(17): p. 6374-9.
15. Giannoukakis, N., et al., *Phase I (safety) study of autologous tolerogenic dendritic cells in type 1 diabetic patients*. Diabetes Care, 2011. 34(9): p. 2026-32.
16. Krampera, M., et al., *Bone marrow mesenchymal stem cells inhibit the response of naive and memory antigen-specific T cells to their cognate peptide*. Blood, 2003. 101(9): p. 3722-9.
17. Opitz, C. A., et al., *Toll-like receptor engagement enhances the immunosuppressive properties of human bone marrow-derived mesenchymal stem cells by inducing indoleamine-2,3-dioxygenase-1 via interferon-beta and protein kinase R*. Stem Cells, 2009. 27(4): p. 909-19.
18. Fan, H., et al., *Pre-treatment with IL-1beta enhances the efficacy of MSC transplantation in DSS-induced colitis*. Cell Mol Immunol, 2012. 9(6): p. 473-81.
19. Duijvestein, M., et al., *Pretreatment with interferon-gamma enhances the therapeutic activity of mesenchymal stromal cells in animal models of colitis*. Stem Cells, 2011. 29(10): p. 1549-58.
20. Krampera, M., et al., *Role for interferon-gamma in the immunomodulatory activity of human bone marrow mesenchymal stem cells*. Stem Cells, 2006. 24(2): p. 386-98.
21. Polchert, D., et al., *IFN-gamma activation of mesenchymal stem cells for treatment and prevention of graft versus host disease*. Eur J Immunol, 2008. 38(6): p. 1745-55.
22. Groh, M. E., et al., *Human mesenchymal stem cells require monocyte-mediated activation to suppress alloreactive T cells*. Exp Hematol, 2005. 33(8): p. 928-34.
23. Bartholomew, A., et al., *Mesenchymal stem cells suppress lymphocyte proliferation in vitro and prolong skin graft survival in vivo*. Exp Hematol, 2002. 30(1): p. 42-8.
24. Beggs, K. J., et al., *Immunologic consequences of multiple, high-dose administration of allogeneic mesenchymal stem cells to baboons*. Cell Transplant, 2006. 15(8-9): p. 711-21.
25. Tse, W. T., et al., *Suppression of allogeneic T-cell proliferation by human marrow stromal cells: implications in transplantation*. Transplantation, 2003. 75(3): p. 389-97.
26. Maitra, B., et al., *Human mesenchymal stem cells support unrelated donor hematopoietic stem cells and suppress T-cell activation*. Bone Marrow Transplant, 2004. 33(6): p. 597-604.
27. Rasmusson, I., et al., *Mesenchymal stem cells inhibit the formation of cytotoxic T lymphocytes, but not activated cytotoxic T lymphocytes or natural killer cells*. Transplantation, 2003. 76(8): p. 1208-13.
28. Angoulvant, D., et al., *Human mesenchymal stem cells suppress induction of cytotoxic response to alloantigens*. Biorheology, 2004. 41(3-4): p. 469-76.

29. Le Blanc, K., et al., *Mesenchymal stem cells inhibit the expression of CD25 (interleukin-2 receptor) and CD38 on phytohaemagglutinin-activated lymphocytes.* Scand J Immunol, 2004. 60(3): p. 307-15.

30. Glennie, S., et al., *Bone marrow mesenchymal stem cells induce division arrest anergy of activated T cells.* Blood, 2005. 105(7): p. 2821-7.

31. Kim, J. A., et al., *The inhibition of T-cells proliferation by mouse mesenchymal stem cells through the induction of p16INK4A-cyclin D1/cdk4 and p21waf1, p27kip1-cyclin E/cdk2 pathways.* Cell Immunol, 2007. 245(1): p. 16-23.

32. Zappia, E., et al., *Mesenchymal stem cells ameliorate experimental autoimmune encephalomyelitis inducing T-cell anergy.* Blood, 2005. 106(5): p. 1755-61.

33. Wang, Q., et al., *Murine bone marrow mesenchymal stem cells cause mature dendritic cells to promote T-cell tolerance.* Scand J Immunol, 2008. 68(6): p. 607-15.

34. Plumas, J., et al., *Mesenchymal stem cells induce apoptosis of activated T cells.* Leukemia, 2005. 19(9): p. 1597-604.

35. Lim, J. H., et al., *Immunomodulation of delayed-type hypersensitivity responses by mesenchymal stem cells is associated with bystander T cell apoptosis in the draining lymph node.* J Immunol, 2010. 185(7): p. 4022-9.

36. Rasmusson, I., et al., *Mesenchymal stem cells inhibit lymphocyte proliferation by mitogens and alloantigens by different mechanisms.* Exp Cell Res, 2005. 305(1): p. 33-41.

37. Xu, G., et al., *Immunosuppressive properties of cloned bone marrow mesenchymal stem cells.* Cell Res, 2007. 17(3): p. 240-8.

38. English, K., et al., *Cell contact, prostaglandin E(2) and transforming growth factor beta 1 play non-redundant roles in human mesenchymal stem cell induction of CD4+ CD25(High) forkhead box P3+ regulatory T cells.* Clin Exp Immunol, 2009. 156(1): p. 149-60.

39. Spaggiari, G. M., et al., *MSCs inhibit monocyte-derived DC maturation and function by selectively interfering with the generation of immature DCs: central role of MSC-derived prostaglandin E2.* Blood, 2009. 113(26): p. 6576-83.

40. Yanez, R., et al., *Prostaglandin E2 plays a key role in the immunosuppressive properties of adipose and bone marrow tissue-derived mesenchymal stromal cells.* Exp Cell Res, 2010. 316(19): p. 3109-23.

41. Zafranskaya, M., et al., *PGE2 Contributes to In vitro MSC-Mediated Inhibition of Non-Specific and Antigen-Specific T Cell Proliferation in MS Patients.* Scand J Immunol, 2013. 78(5): p. 455-62.

42. Nasef, A., et al., *Identification of IL-10 and TGF-beta transcripts involved in the inhibition of T-lymphocyte proliferation during cell contact with human mesenchymal stem cells.* Gene Expr, 2007. 13(4-5): p. 217-26.

43. Magatti, M., et al., *Human amnion mesenchyme harbors cells with allogeneic T-cell suppression and stimulation capabilities.* Stem Cells, 2008. 26(1): p. 182-92.

44. El Haddad, N., et al., *Mesenchymal stem cells express serine protease inhibitor to evade the host immune response.* Blood, 2011. 117(4): p. 1176-83.

45. Sato, K., et al., *Nitric oxide plays a critical role in suppression of T-cell proliferation by mesenchymal stem cells.* Blood, 2007. 109(1): p. 228-34.

46. Oh, I., et al., *Interferon-gamma and NF-kappaB mediate nitric oxide production by mesenchymal stromal cells.* Biochem Biophys Res Commun, 2007. 355(4): p. 956-62.

47. Ren, G., et al., *Mesenchymal stem cell-mediated immunosuppression occurs via concerted action of chemokines and nitric oxide.* Cell Stem Cell, 2008. 2(2): p. 141-50.

48. DelaRosa, O., et al., *Requirement of IFN-gamma-mediated indoleamine 2,3-dioxygenase expression in the modulation of lymphocyte proliferation by human adipose-derived stem cells.* Tissue Eng Part A, 2009. 15(10): p. 2795-806.

49. Tipnis, S., C. Viswanathan, and A. S. Majumdar, *Immunosuppressive properties of human umbilical cord-derived mesenchymal stem cells: role of B7-H1 and IDO.* Immunol Cell Biol, 2010. 88(8): p. 795-806.

50. Ge, W., et al., *Regulatory T-cell generation and kidney allograft tolerance induced by mesenchymal stem cells associated with indoleamine 2,3-dioxygenase expression.* Transplantation, 2010. 90(12): p. 1312-20.

51. Francois, M., et al., *Human MSC suppression correlates with cytokine induction of indoleamine 2,3-dioxygenase and bystander M2 macrophage differentiation.* Mol Ther, 2012. 20(1): p. 187-95.

52. Sattler, C., et al., *Inhibition of T-cell proliferation by murine multipotent mesenchymal stromal cells is mediated by CD39 expression and adenosine generation.* Cell Transplant, 2011. 20(8): p. 1221-30.

53. Saldanha-Araujo, F., et al., *Mesenchymal stromal cells up-regulate CD39 and increase adenosine production to suppress activated T-lymphocytes.* Stem Cell Res, 2011. 7(1): p. 66-74.

54. Xue, Q., et al., *The negative co-signaling molecule b7-h4 is expressed by human bone marrow-derived mesenchymal stem cells and mediates its T-cell modulatory activity.* Stem Cells Dev, 2010. 19(1): p. 27-38.

55. Gieseke, F., et al., *Human multipotent mesenchymal stromal cells use galectin-1 to inhibit immune effector cells.* Blood, 2010. 116(19): p. 3770-9.

56. Chabannes, D., et al., *A role for heme oxygenase-1 in the immunosuppressive effect of adult rat and human mesenchymal stem cells.* Blood, 2007. 110(10): p. 3691-4.

57. Mougiakakos, D., et al., *The impact of inflammatory licensing on heme oxygenase-1-mediated induction of regulatory T cells by human mesenchymal stem cells.* Blood, 2011. 117(18): p. 4826-35.

58. Augello, A., et al., *Bone marrow mesenchymal progenitor cells inhibit lymphocyte proliferation by activation of the programmed death 1 pathway.* Eur J Immunol, 2005. 35(5): p. 1482-90.

59. Sheng, H., et al., *A critical role of IFNgamma in priming MSC-mediated suppression of T cell proliferation through up-regulation of B7-H1.* Cell Res, 2008. 18(8): p. 846-57.

60. Luz-Crawford, P., et al., *Mesenchymal stem cells repress Th17 molecular program through the PD-1 pathway.* PLoS One, 2012. 7(9): p. e45272.

61. Akiyama, K., et al., *Mesenchymal-stem-cell-induced immunoregulation involves FAS-ligand-/FAS-mediated T cell apoptosis.* Cell Stem Cell, 2012. 10(5): p. 544-55.

62. Gu, Y. Z., et al., *Different roles of PD-L1 and FasL in immunomodulation mediated by human placenta-derived mesenchymal stem cells.* Hum Immunol, 2013. 74(3): p. 267-76.

63. Najar, M., et al., *Characterization and functionality of the CD200-CD200R system during mesenchymal stromal cell interactions with T-lymphocytes.* Immunol Lett, 2012. 146(1-2): p. 50-6.

64. Batten, P., et al., *Human mesenchymal stem cells induce T cell anergy and downregulate T cell allo-responses via the TH2 pathway: relevance to tissue engineering human heart valves.* Tissue Eng, 2006. 12(8): p. 2263-73.

65. Lu, X., et al., *Immunomodulatory effects of mesenchymal stem cells involved in favoring type 2 T cell subsets.* Transpl Immunol, 2009. 22(1-2): p. 55-61.

66. Zanone, M. M., et al., *Human mesenchymal stem cells modulate cellular immune response to islet antigen glutamic acid decarboxylase in type 1 diabetes.* J Clin Endocrinol Metab, 2010. 95(8): p. 3788-97.

67. Ko, E., et al., *Mesenchymal stem cells inhibit the differentiation of CD4+ T cells into interleukin-17-secreting T cells.* Acta Haematol, 2008. 120(3): p. 165-7.

68. Rafei, M., et al., *Mesenchymal stromal cells ameliorate experimental autoimmune encephalomyelitis by inhibiting CD4 Th17 T cells in a CC chemokine ligand 2-dependent manner.* J Immunol, 2009. 182(10): p. 5994-6002.

69. Tatara, R., et al., *Mesenchymal stromal cells inhibit Th17 but not regulatory T-cell differentiation. Cytotherapy,* 2011. 13(6): p. 686-94.

70. Duffy, M. M., et al., *Mesenchymal stem cell inhibition of T-helper 17 cell-differentiation is triggered by cell-cell contact and mediated by prostaglandin E2 via the EP4 receptor.* Eur J Immunol, 2011. 41(10): p. 2840-51.

71. Luz-Crawford, P., et al., *Mesenchymal stem cells generate a CD4+CD25+Foxp3+ regulatory T cell population during the differentiation process of Th1 and Th17 cells.* Stem Cell Res Ther, 2013. 4(3): p. 65.

72. Kota, D. J., et al., *TSG-6 produced by hMSCs delays the onset of autoimmune diabetes by suppressing Th1 development and enhancing tolerogenicity.* Diabetes, 2013. 62(6): p. 2048-58.

73. Del Papa, B., et al., *Notch1 modulates mesenchymal stem cells mediated regulatory T-cell induction.* Eur J Immunol, 2013. 43(1): p. 182-7.

74. Maccario, R., et al., *Interaction of human mesenchymal stem cells with cells involved in alloantigen-specific immune response favors the differentiation of CD4+ T-cell subsets expressing a regulatory/suppressive phenotype.* Haematologica, 2005. 90(4): p. 516-25.

75. Prevosto, C., et al., *Generation of CD4+ or CD8+ regulatory T cells upon mesenchymal stem cell-lymphocyte interaction.* Haematologica, 2007. 92(7): p. 881-8.

76. Di Ianni, M., et al., *Mesenchymal cells recruit and regulate T regulatory cells.* Exp Hematol, 2008. 36(3): p. 309-18.

77. Casiraghi, F., et al., *Pretransplant infusion of mesenchymal stem cells prolongs the survival of a semiallogeneic heart transplant through the generation of regulatory T cells.* J Immunol, 2008. 181(6): p. 3933-46.

78. Boumaza, I., et al., *Autologous bone marrow-derived rat mesenchymal stem cells promote PDX-1 and insulin expression in the islets, alter T cell cytokine pattern and preserve regulatory T cells in the periphery and induce sustained normoglycemia.* J Autoimmun, 2009. 32(1): p. 33-42.

79. Ye, Z., et al., *Immunosuppressive effects of rat mesenchymal stem cells: involvement of CD4+CD25+ regulatory T cells.* Hepatobiliary Pancreat Dis Int, 2008. 7(6): p. 608-14.

80. Madec, A. M., et al., *Mesenchymal stem cells protect NOD mice from diabetes by inducing regulatory T cells.* Diabetologia, 2009. 52(7): p. 1391-9.

81. Melief, S. M., et al., *Multipotent stromal cells induce human regulatory T cells through a novel pathway involving skewing of monocytes toward anti-inflammatory macrophages.* Stem Cells, 2013. 31(9): p. 1980-91.

82. Zhang, X. Y., et al., *Lentiviral vectors for sustained transgene expression in human bone marrow-derived stromal cells.* Mol Ther, 2002. 5(5 Pt 1): p. 555-65.

83. Kyriakou, C. A., et al., *Human mesenchymal stem cells (hMSCs) expressing truncated soluble vascular endothelial growth factor receptor (tsFlk-1) following lentiviral-mediated gene transfer inhibit growth of Burkitt's lymphoma in a murine model.* J Gene Med, 2006. 8(3): p. 253-64.

84. Worsham, D. N., et al., *In vivo gene transfer into adult stem cells in unconditioned mice by in situ delivery of a lentiviral vector.* Mol Ther, 2006. 14(4): p. 514-24.

85. Rabin, N., et al., *A new xenograft model of myeloma bone disease demonstrating the efficacy of human mesenchymal stem cells expressing osteoprotegerin by lentiviral gene transfer.* Leukemia, 2007. 21(10): p. 2181-91.

86. Kallifatidis, G., et al., *Improved lentiviral transduction of human mesenchymal stem cells for therapeutic intervention in pancreatic cancer.* Cancer Gene Ther, 2008. 15(4): p. 231-40.

87. Meyerrose, T. E., et al., *Lentiviral-transduced human mesenchymal stem cells persistently express therapeutic levels of enzyme in a xenotransplantation model of human disease.* Stem Cells, 2008. 26(7): p. 1713-22.

88. McGinley, L., et al., *Lentiviral vector mediated modification of mesenchymal stem cells & enhanced survival in an in vitro model of ischaemia.* Stem Cell Res Ther, 2011. 2(2): p. 12.

89. Liang, X., et al., *Human bone marrow mesenchymal stem cells expressing SDF-1 promote hematopoietic stem cell function of human mobilised peripheral blood CD34+ cells in vivo and in vitro.* Int J Radiat Biol, 2010. 86(3): p. 230-7.

90. Hamidouche, Z., et al., *Autocrine fibroblast growth factor 18 mediates dexamethasone-induced osteogenic differentiation of murine mesenchymal stem cells.* J Cell Physiol, 2010. 224(2): p. 509-15.

91. Glavaski-Joksimovic, A., et al., *Glial cell line-derived neurotrophic factor-secreting genetically modified human bone marrow-derived mesenchymal stem cells promote recovery in a rat model of Parkinson's disease.* J Neurosci Res, 2010. 88(12): p. 2669-81.

92. Liu, A. M., et al., *Umbilical cord-derived mesenchymal stem cells with forced expression of hepatocyte growth factor enhance remyelination and functional recovery in a rat intracerebral hemorrhage model.* Neurosurgery, 2010. 67(2): p. 357-65; discussion 365-6.

93. Yu, Y. S., et al., *AKT-modified autologous intracoronary mesenchymal stem cells prevent remodeling and repair in swine infarcted myocardium.* Chin Med J (Engl), 2010. 123(13): p. 1702-8.

94. Mueller, L. P., et al., *TRAIL-transduced multipotent mesenchymal stromal cells (TRAIL-MSC) overcome TRAIL resistance in selected CRC cell lines in vitro and in vivo.* Cancer Gene Ther, 2011. 18(4): p. 229-39.

95. Yan, C., et al., *Suppression of orthotopically implanted hepatocarcinoma in mice by umbilical cord-derived mesenchymal stem cells with sTRAIL gene expression driven by AFP promoter.* Biomaterials, 2014. 35(9): p. 3035-43.

96. Deng, Q., et al., *TRAIL-secreting mesenchymal stem cells promote apoptosis in heat-shock-treated liver cancer cells and inhibit tumor growth in nude mice.* Gene Ther, 2014. 21(3): p. 317-27.

97. Sage, E. K., et al., *Systemic but not topical TRAIL-expressing mesenchymal stem cells reduce tumour growth in malignant mesothelioma.* Thorax, 2014. 69(7): p. 638-47.

98. Lian, W. S., et al., *In vivo therapy of myocardial infarction with mesenchymal stem cells modified with prostaglandin I synthase gene improves cardiac performance in mice.* Life Sci, 2011. 88(9-10): p. 455-64.

99. Maijenburg, M. W., et al., *Nuclear receptors Nur77 and Nurr1 modulate mesenchymal stromal cell migration.* Stem Cells Dev, 2012. 21(2): p. 228-38.

100. Harper, M. M., et al., *Transplantation of BDNF-secreting mesenchymal stem cells provides neuroprotection in chronically hypertensive rat eyes.* Invest Ophthalmol Vis Sci, 2011. 52(7): p. 4506-15.

101. Zou, D., et al., *In vitro study of enhanced osteogenesis induced by HIF-1alpha-transduced bone marrow stem cells.* Cell Prolif, 2011. 44(3): p. 234-43.

102. Saito, S., et al., *Mesenchymal stem cells stably transduced with a dominant-negative inhibitor of CCL2 greatly attenuate bleomycin-induced lung damage.* Am J Pathol, 2011. 179(3): p. 1088-94.

103. Seo, K. W., et al., *Anti-tumor effects of canine adipose tissue-derived mesenchymal stromal cell-based interferon-beta gene therapy and cisplatin in a mouse melanoma model.* Cytotherapy, 2011. 13(8): p. 944-55.

104. Yang, H. M., et al., *Enhancement of the immunosuppressive effect of human adipose tissue-derived mesenchymal stromal cells through HLA-G1 expression.* Cytotherapy, 2012. 14(1): p. 70-9.

105. Liang, X. J., et al., *Differentiation of human umbilical cord mesenchymal stem cells into hepatocyte-like cells by hTERT gene transfection in vitro.* Cell Biol Int, 2012. 36(2): p. 215-21.

106. Fei, S., et al., *The antitumor effect of mesenchymal stem cells transduced with a lentiviral vector expressing cytosine deaminase in a rat glioma model.* J Cancer Res Clin Oncol, 2012. 138(2): p. 347-57.

107. Jaganathan, B. G. and D. Bonnet, *Human mesenchymal stromal cells senesce with exogenous OCT4.* Cytotherapy, 2012. 14(9): p. 1054-63.

108. Han, S. H., et al., *Effect of ectopic OCT4 expression on canine adipose tissue-derived mesenchymal stem cell proliferation.* Cell Biol Int, 2014. 38(10): p. 1163-73.

109. Shangguan, L., et al., *Inhibition of TGF-beta/Smad signaling by BAMBI blocks differentiation of human mesenchymal stem cells to carcinoma-associated fibroblasts and abolishes their protumor effects.* Stem Cells, 2012. 30(12): p. 2810-9.

110. Kearns-Jonker, M., et al., *Genetically Engineered Mesenchymal Stem Cells Influence Gene Expression in Donor Cardiomyocytes and the Recipient Heart.* J Stem Cell Res Ther, 2012. S1.

111. Ma, G. L., et al., [*Study of inhibiting and killing effects of transgenic LIGHT human umbilical cord blood mesenchymal stem cells on stomach cancer*]. Zhonghua Wei Chang Wal Ke Za Zhi, 2012. 15(11): p. 1178-81.

112. Huang, F., et al., *Mesenchymal stem cells modified with miR-126 release angiogenic factors and activate Notch ligand Delta-like-4, enhancing ischemic angiogenesis and cell survival.* Int J Mol Med, 2013. 31(2): p. 484-92.

113. Huang, F., et al., *Overexpression of miR-126 promotes the differentiation of mesenchymal stem cells toward endothelial cells via activation of PI3K/Akt and MAPK/ERK pathways and release of paracrine factors.* Biol Chem, 2013. 394(9): p. 1223-33.

114. Fang, Z., et al., *Differentiation of GFP-Bcl-2-engineered mesenchymal stem cells towards a nucleus pulposus-like phenotype under hypoxia in vitro.* Biochem Biophys Res Commun, 2013. 432(3): p. 444-50.

115. Madonna, R., et al., *Transplantation of mesenchymal cells rejuvenated by the overexpression of telomerase and myocardin promotes revascularization and tissue repair in a murine model of hindlimb ischemia.* Circ Res, 2013. 113(7): p. 902-14.

116. Zang, Y., et al., [*Influence of CXCR4 overexpressed mesenchymal stem cells on hematopoietic recovery of irradiated mice*]. Zhongguo Shi Yan Xue Ye Xue Za Zhi, 2013. 21(5): p. 1261-5.

117. Cao, Z., et al., *Protective effects of mesenchymal stem cells with CXCR4 up-regulation in a rat renal transplantation model.* PLoS One, 2013. 8(12): p. e82949.

118. Liu, S., et al., *Overexpression of Wnt11 promotes chondrogenic differentiation of bone marrow-derived mesenchymal stem cells in synergism with TGF-beta.* Mol Cell Biochem, 2014. 390(1-2): p. 123-31.

119. Yin, N., et al., *Islet-1 promotes the cardiac-specific differentiation of mesenchymal stem cells through the regulation of histone acetylation.* Int J Mol Med, 2014. 33(5): p. 1075-82.

120. Hajizadeh-Sikaroodi, S., et al., *Lentiviral Mediating Genetic Engineered Mesenchymal Stem Cells for Releasing IL-27 as a Gene Therapy Approach for Autoimmune Diseases.* Cell J, 2014. 16(3): p. 255-62.

121. He, H., et al., *Mesenchymal Stem Cells Overexpressing Angiotensin-Converting Enzyme 2 Rescue Lipopolysaccharide-Induced Lung Injury.* Cell Transplant, 2014.

122. Ma, H. C., et al., *Targeted migration of mesenchymal stem cells modified with CXCR4 to acute failing liver improves liver regeneration.* World J Gastroenterol, 2014. 20(40): p. 14884-94.

123. Yang, J. X., et al., *CXCR4 receptor overexpression in mesenchymal stem cells facilitates treatment of acute lung injury in rats.* J Biol Chem, 2015. 290(4): p. 1994-2006.

124. Zhu, Y., et al., *Mesenchymal stem cell-based NK4 gene therapy in nude mice bearing gastric cancer xenografts.* Drug Des Devel Ther, 2014. 8: p. 2449-62.

Although the present disclosure and its advantages have been described in detail, it should be understood that various changes, substitutions and alterations can be made herein without departing from the spirit and scope of the design as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A method of enhancing survival of allogeneic or autologous insulin-producing cells in an individual, comprising the steps of administering a composition comprising an effective amount of fibroblasts prior to, concurrent with, and/or subsequent to transplantation of said allogeneic or autologous insulin-producing cells in the individual; wherein said fibroblasts are CD73-positive.

2. The method of claim 1, wherein the fibroblasts are allogeneic to the individual.

3. The method of claim 1, wherein the allogeneic insulin-producing cells are derived from a pancreatic donor.

4. The method of claim 1, wherein the allogeneic insulin-producing cells are comprised of islet cell mass.

5. The method of claim 1, wherein said allogeneic insulin producing cells are derived from in vitro differentiation from a population of progenitor cells.

6. The method of claim 1, wherein the composition further comprises endothelial progenitor cells (EPCs).

7. The method of claim 6, wherein said EPCs express markers selected from the group consisting of: a) flk-1; b) CD31; c) CD34; d) CD133; f) PDGF-R; g) hTERT; and h) a combination thereof.

8. The method of claim 6, wherein the EPCs are derived by a method comprising the steps of: (i) isolating a mammalian cellular population; (ii) enriching for a subpopulation of the cells of step (i) that expresses a CD45 phenotypic profile; (iii) enriching for a subpopulation of the CD45$^-$ cells derived from step (ii) that express a CD34$^+$ phenotypic profile; and (iv) isolating the subpopulation of CD34$^+$ cells derived from step (iii) that express a CD31$^{lo/-}$ phenotypic profile, to thereby isolate the endothelial progenitor cells.

9. The method of claim 6, wherein the EPCs are derived from placental tissue, bone marrow, adipose tissue, omentum, or a combination thereof.

* * * * *